United States Patent
Srivastava

(12) 
(10) Patent No.: US 6,451,316 B1
(45) Date of Patent: Sep. 17, 2002

(54) METHODS FOR GENERATING ANTIGEN-REACTIVE T CELLS IN VITRO

(75) Inventor: Pramod K. Srivastava, Avon, CT (US)

(73) Assignee: University of Conneticut Health Center, Farmington, CT (US)

( * ) Notice: Subject to any disclaimer, the term of this patent is extended or adjusted under 35 U.S.C. 154(b) by 0 days.

(21) Appl. No.: 09/166,401

(22) Filed: Oct. 5, 1998

(51) Int. Cl.$^7$ ............... G01N 33/53; G01N 33/567; C12N 5/06; C12N 5/08; A61K 39/385

(52) U.S. Cl. ............ 424/193.1; 435/7.2; 435/7.21; 435/7.24; 435/325; 435/354; 435/366; 435/355; 435/372.3; 435/373; 435/384; 530/350

(58) Field of Search .............. 530/350; 424/193.1; 435/7.2, 7.21, 7.24, 325, 354, 355, 366, 372.3, 373, 384

(56) References Cited

U.S. PATENT DOCUMENTS 4,690,915 A    9/1987    Rosenberg

FOREIGN PATENT DOCUMENTS

| | | |
|---|---|---|
| DE | 196 02 985 A1 | 7/1997 |
| WO | WO 89/12455 | 12/1989 |
| WO | WO 94/29459 | 12/1994 |
| WO | WO 95/24923 | 9/1995 |
| WO | WO 97/06685 | 2/1997 |
| WO | WO 97/06821 | 2/1997 |
| WO | WO 97/06828 | 2/1997 |
| WO | WO 97/26910 | 7/1997 |
| WO | WO 98/15616 | 4/1998 |

OTHER PUBLICATIONS

Anichini et al., 1987, "Clonal analysis of the cytolytic T–cell response to human tumors", Immunol. Today 8:385–389.
Barrios et al., 1994, "Specificity of antibodies induced after immunization of mice with the mycobacterial heat shock protein of 65kD", Clin. Exp. Immunol., 98:224–228.
Barrios et al., 1994, "Heat shock protein as carrier molecules: in vivo helper effect mediated by *Escherichia coli* GroEL and DnaK proteins requires cross–linking with antigen", Clin. Exp. Immunol., 98:229–233.
Barrios, 1992, "Mycobacterial heat shock proteins as carrier molecules. II: the use of 70kDa mycobacterial heat–shock protein as carrier for conjugated vaccines can circumvent the need for adjuvants and Bacillus Calmette Guerin priming", Eur. J. Immunol. 22:1365–1372.
Bartlett, 1972, "Effect of host immunity on the antigenic strength of primary tumors", J Natl Cancer Inst 49:493–504.
Berke, 1995, "The CTL's kiss of death", Cell 81:9–12.
Bevan, 1995, "Antigen presentation to cytotoxic T–lymphocytes in vivo", J. Exp. Med. 182:639–641.
Blachere et al., 1993, "Heat shock protein vaccines against", J. Immunother. 14:352–356.

Blachere and Srivastava, 1993, "Immunization with GP96 heat shock proteins isolated from tumors or influenza virus infected cells elicits MHC–restricted antigen–specific cytotoxic T lymphocytes against the corresponding cells/antigens", J. Cell. Biochem. Keystone Sym. NZ502, p. 124.
Cohen S., 1987, "Infection against infectious diseases", Basic and Clinical Immunology (Appleton & Lange, Norwalk) pp. 669–689.
De Bruijn et al., 1991, "Peptide loading of empty major histocompatibility complex molecules on RMA–S cells allows the induction of primary cytotoxic T lymphocyte response", Eur. J. Immunol. 21:2963–2970.
De Bruijn et al., 1992, "Mechanisms of induction of primary virus–specific cytotoxic T lymphocyte responses", Eur. J. Immunol. 22:3013–3020.
De Bruijn et al., 1995, "Phagocyte–induced antigen–specific activation of unprimed CD8+ T cells in vitro", Eur. J. Immunol. 25:1274–1285.
Dozmorov & Miller, 1997, "In vitro production of antigen–specific T cells from unprimed mice: role of dexamethasone and anti–IL–10 antibodies", Cell. Immunol. 178:187–196.
Engers et al., 1975, "Generation of cytotoxic T lymphocytes in vitro", J. Immunol. 115:356–360.
Falk et al., 1990, "Cellular peptide composition governed by major histocompatibility complex class I molecules", Nature 348:248–251.
Falk et al., 1991, "Allele–specific motifs revealed by sequencing of self–peptides eluted from MHC molecules", Nature 351:290–296.
Fathman et al., 1989, "Long–term culture of immunocompetent cells", Fundamental Immunology (Raven Press Ltd., New York) pp. 803–815.
Feldweg and Srivastava, 1993, "Evidence for biochemical heterogeneity of GP96 heat shock protein/tumor rejection antigen", J. Cell. Biochem. Suppl., Abstract NZ 108.
Fossati et al., 1982, "Lysis of autologous human melanoma cells by in vitro allosensitized peripheral blood lymphocytes", Cancer Immunol. Immunother. 14:99–104.
Gartner et al., 1986, "The role of mononuclear phagocytes in HTLV–III/LAV infection", Science 233:215–217.

(List continued on next page.)

*Primary Examiner*—Geetha P. Bansal
(74) *Attorney, Agent, or Firm*—Pennie & Edmonds LLP

(57) ABSTRACT

The present invention provides methods for generating antigen-reactive T cells in vitro comprising priming immune cells and incubating the primed immune cells in vitro with a non-covalent complex of an heat shock protein and an antigenic molecule. The present invention further relates to methods for generating antigen-reactive CD4+ T cells for immunotherapy. Methods and compositions are also disclosed for the treatment and prevention of cancer or infectious disease in a subject comprising administering to the subject MHC matched antigen-reactive T cells that are generated in vitro by the present methods.

35 Claims, 10 Drawing Sheets

OTHER PUBLICATIONS

Figure 1:
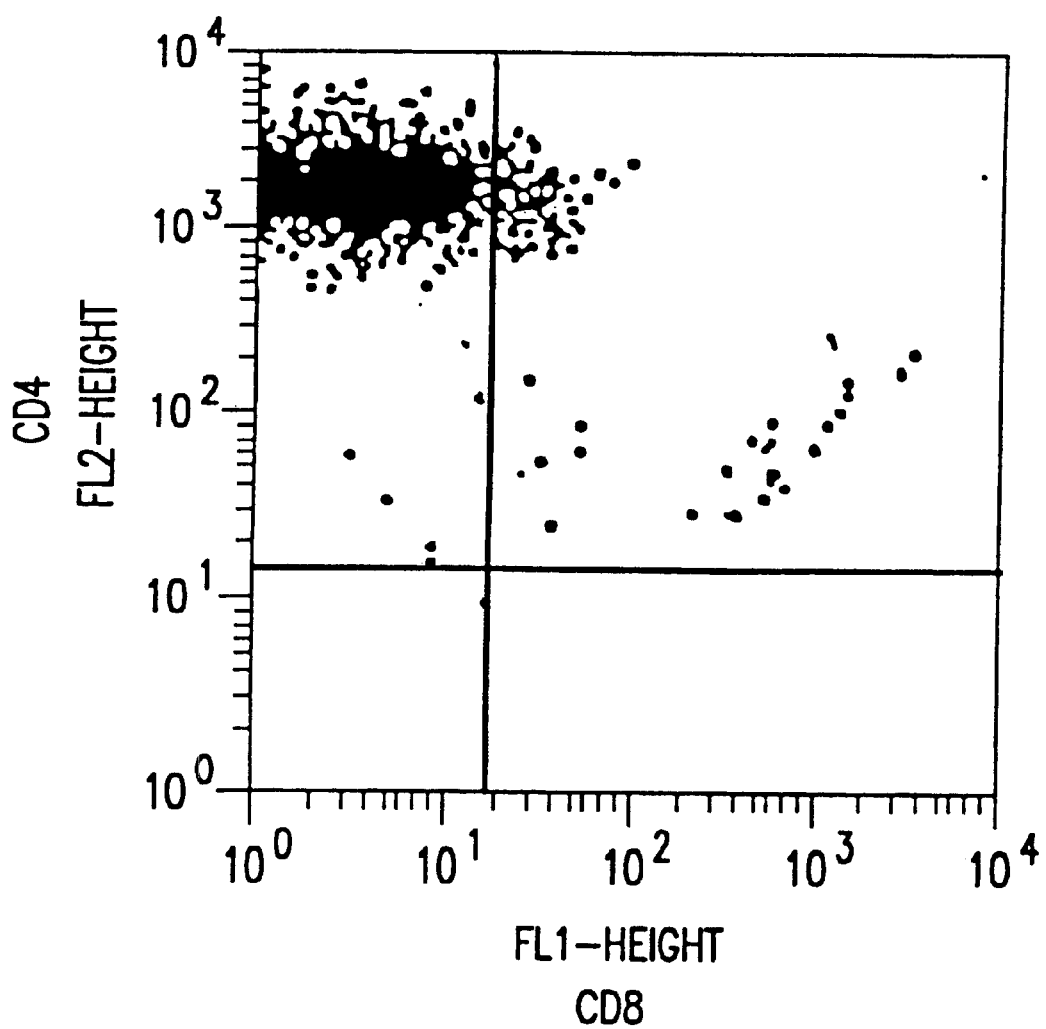

Greenberg et al., 1983, "Therapy of established tumors by adoptive transfer of T lymphocytes", in "Basic and clinical tumor immunology", ed. Herbermann RR, Martinus Nijhoff Publishers, Boston, pp. 301–335.

Greenberg, 1987, "Tumor immunology", Basic and Clinical Immunology (Appleton and Lange, Norwalk) pp. 186–196.

Grimm et al., 1982, "Lymphokine–activated killer cell phenomenon", J. Exp. Med. 155:1823–1841.

Heike et al., 1998, "Stimulation of HLA–A–A2 restricted peptide–specific anti–melanoma CTL by heat shock protein GP96 derived from the autologous melanoma", International Symposium by the Cancer Research Institute, Oct. 7–9:M13.

Herin et al., 1987, "Production of stable cytolytic T–cell clones directed against autologous human melanoma", Int. J. Cancer 39:390–396.

Hersey et al., 1981, "Induction of cytotoxic activity in human lymphocytes against autologous and allogeneic melanoma cells in vitro by culture with interleukin 2", Int. J. Cancer 28:695–703.

Holladay et al., 1996, "Autologous tumor cell vaccination combined with adoptive cellular immunotherapy in patients with grade III/IV astrocytoma", J. Neural Oncol. 27:179–189.

Houbiers et al., 1993, "In vitro induction of human cytotoxic T lymphocyte responses against peptides of mutant and wild–type p 53"Eur. J. Immunol. 26:2072–2077.

Inaba et al., 1987, "Direct activation of CD8+ cytotoxic T lymphocytes by dendritic cells", J. Exp. Med. 166:182–194.

Klein et al., 1960, "Demonstration of resistance against methylcholanthrene–induced sarcomas in the primary Autochthonous Host", Cancer Res. 20:1561–1572.

Kobayashi et al., 1998, "CD4+ T cells from peripheral blood of a melanoma patient recognize peptides derived from non–mutated tyrosinase", Cancer Res. 58:296–300.

Konishi et al., 1995, "Japanese encephalitis virus–specific proliferative responses of human peripheral blood T lymphocytes", Am. J. Trop. Med. Hyg. 53(3), 278–283.

Lakey et al., 1997, "Identification of a peptide binding protein that plays a role in antigen presentation", Proc. Natl. Acad. Sci. USA 84:1659–1663.

Lanzavecchia, 1996, "Mechanisms of antigen uptake for presentation", Curr. Opin. Immunol. 8:348–354.

Lanzavecchia, 1993, "Identifying strategies for immune intervention", Science 260:937–944.

Levy, 1991, "ATP is require for in vivo assembly of MHC class I antigens but not for transfer of peptides across the ER membrane", Cell 67:265–274.

Li and Srivastava, 1993, "Tumor rejection antigen gp96/grp94 is an ATPase: implications for protein folding and antigen presentation", EMBO J. 12:3143–3151.

Lindquist and Craig, 1988, "The heat–shock proteins", Ann. Rev. Genet. 22:631–677.

Luescher et al., 1991, "Specific binding of antigenic peptides cell–associated MHC class I molecules", Nature 351:72–77.

Lussow et al., 1991, "Mycobacterial heat–shock proteins as carrier molecules", Eur. J. Immunol. 21:2297–2302.

Macatonia et al., 1989, "Primary stimulation by dendritic cells induces antiviral proliferative and cytotoxic T–cell responses in vitro", J. Exp. Med. 169:1255–1264.

Matsutake T. & Srivastava P., 1998, "Gp96 Chaperoned peptides gain access to the MHC lass II presentation pathway", International Symposium by the Cancer Research Institute, Oct. 5–9:P1–13.

Melief and Kast, 1992, "Lessons from T cell responses to virus induced tumors for cancer eradication in general", Cancer Surveys vol. 13: A New Look at Tumor Immunology, Imperial Cancer Research Fund pp. 81–99.

Monach et al., 1995, "A unique tumor antigen produced by a single amino acid substitution", Immunity 2:45–59.

Moore et al.,1988, "Introduction of soluble protein into the Class I pathway of Antigen processing and presentation", Cell 54(6):777–785.

Mule et al., 1984, "Adoptive Immunotherapy of established pulmonary metastases with LAK cells and recombinant interleukin", Science 225:1487–1489.

Nair et al., 1997, "Antigen–presenting cells pulsed with unfractionated tumor–derived peptides are potent tumor vaccines", Eur. J. Immunol. 27:589–597.

Nair et al., 1992, "Class I restricted CTL recognition of a soluble protein delivered by liposomes containing lipophilic polylysines", J. Immunol. Methods 152:237–243.

Old et al., 1962, "Antigenic properties of chemically induced tumors", Ann. N.Y. Acad. Sci. 101:80–106.

Palladino et al., 1987, "Expression of a shared tumor–specific antigen by two chemically induced BALB/c sarcomas", Cancer Res. 47:5074–5079.

Rosenberg et al., 1988, "A progress report on the treatment of 157 patients with advanced cancer using lymphokine–activated killer cells and interleukin–2 or high–dose interleukin–2 alone", New Engl. J. Med. 316:889–897.

Rosenberg et al., 1988, "Use of tumor–infiltrating lymphocytes and interleukin–2 in the immunotherapy of patients with metastic melanoma", N. Eng. J. Med. 319:1676–1680.

Rotzschke et al., 1990, "Isolation and analysis of naturally processed viral peptide as recognized cytotoxic T cells", Nature 348:248–251.

Rudensky et al., 1991, "Sequence analysis of peptides bound to MHC class II molecules", Nature 353:622–627.

Sallusto and Lanzavecchia, 1994, "Efficient presentation of soluble antigen by cultured human dendritic cells is maintained by granulocyte/macrophage colony–stimulating factor plus interleukin 4 and down regulated by tumor necrosis factor $\alpha$", J. Exp. Med. 179:1109–1118.

Schumacher et al., 1991, "Peptide selection by MHC class I molecules", Nature 350:703–706.

Slovin et al., 1986, "Cellular immune response to human sarcomas: cytotoxic T cell clones reactive with autologous sarcomas", J. Immunol. 9:3042–3048.

Srivastava et al., 1987, "5'–structural analysis of genes encoding polymorphic antigens of chemically induced tumors", Proc. Natl. Acad. Sci. USA 84:3807–3811.

Srivastava et al., 1986, "Tumor rejection antigens of chemically induced sarcomas inbred mice", Proc. Natl. Acad. Sci. USA 83:3407–3411.

Srivastava et al., 1989, "Identification of a human homologue of murine tumor rejection antigen GP96", Cancer Res. 49:1341–1343.

Srivastava and Heike, 1986, "Tumor–specific immunogenicity of stress–induced proteins: convergence of two evolutionary pathways of antigen presentation", Sem. in Immunol. 3:57–64.

Srivastava et al., 1984, "The serologically unique cell surface antigen of zajdela ascitic hepatoma is also its tumor–associated transplantation antigen", Int. J. Cancer 33:417–422.

Srivastava et al., 1994, "Heat shock proteins transfer peptides during antigen processing and CTL priming", Immunogenetics 39:93–98.

Srivastava et al., 1991, "Protein tumor antigens", Curr. Opin. Immunol. 3:654–658.

Srivastava and Maki, 1991, "Stress–induced proteins in immune response to cancer", Microbiol. Immunol. 167:109–123.

Srivastava P. & Old L., 1988, "Individually distinct transplantation antigens of chemically induced mouse tumors", Immunol. Today 9:78–83.

Steel and Nutman, 1998, "Helminth antigens selectively differentiate unsensitized CD45RA+CD4+ T cells in vitro", J. Immunol. 160:351–360.

Suto R. & Srivasta P., 1995, "A mechanism for the specific immunogenicity of heat shock protein–chaperoned peptides", Science 269:1585–1588.

Tamura et al., 1997, "Immunotherapy with autologous tumor–derived heat shock protein preparation", Science 278:117–120.

Tao et al., 1997, "Induction IL–4–producing CD4+ T cells by antigenic peptides altered for TCR binding", J. Immunol 158:4237–44.

Taylor and Cohen, 1992, "Cell–mediated cytotoxicity", Curr. Opin. Immunol. 4:338–343.

Tevethia et al., 1974, "Requirement of thymus–derived θ–positive lymphocytes for rejection of DNA virus (SV40) tumors in mice", J. Immunol. 13:1417–1423.

Topalian et al., 1989, "Tumor–specific cytolysis by lymphocytes infiltrating human melanomas", J. Immunol. 142:3714–3725.

Udono, 1993, "Heat shock proteins HSP70, HSP90 &GP96 elicit tumor –specific immunity to the tumors from which they are isolated", J. Cell. Biochem. Suppl. 17D:113 (Abs. NZ225).

Udono et al., 1993, "Heat shock protein 70–associated peptides elicit specific cancer immunity", J. Exp. Med. 178:1391–1396.

Ullrich et al., 1986, "A mouse tumor–specific transplantation antigen is a heat shock related protein", Proc. Natl. Acad. Sci. USA 83:3121–3125.

Umezu et al., 1993, "Increase in the ability of human cancer cells to induce cytotoxic T lymphocytes by ultraviolet irradiation", Cancer Immunol. Immunother. 37:392–399.

Valitutti et al., 1995, "Serail triggering of many T–cell receptors by a few peptide–MHC complexes", Nature 375:148–151.

Vanbuskirk et al., 1989, "A peptide binding protein having a role in antigen presentation is a member of the HSP70 heat shock family", J. Exp. Med. 170:1799–1809.

Yewdell J. & Bennink J, 1992, "Cell biology of antigen processing and presentation to major histocompatibility complex class I molecule–restricted T Lymphocytes", Adv. Immunol. 52:1–123.

Young, 1990, "Stress proteins and immunology", Ann. Rev. Immunol. 8:401–420.

Zarling et al., 1978, "Generation of cytotoxic T lymphocytes to autologous human leukemia cells by sensitization to pooled allogenic normal cells", Nature 274:269–271.

Zivny et al., "Dengue virus–specific, human CD4+ cytotoxic T lymphocytes generated in short term culture", Viral Immunol. 6(2):143–151.

Naito et al., "Expansion of tumor–specific cytolytic T–lymphocytes using in vitro restimulation with tumor–specific antigen", Cellular Immunol. 108:483–494.

Zinkernagel et al., 1980, "Lymphohemopoeitic origin of the immunogenic, virus–antigen–presenting cells triggering anti–viral–t–cell responses", Clin. Immunol. 15, 565–576.

Blachere et al., 1997, "Heat Shock Protein–Peptide Complexes, Reconstituted In Vitro, Elicit Peptide–Specific Cytotoxic T Lymphocyte Response and Tumor Immunity", J. Exp. Med., 186(3):1315–1322.

METHODS FOR GENERATING ANTIGEN-REACTIVE T CELLS IN VITRO

This invention was made with government support under grant numbers CA44786 and CA64394 awarded by the National Institutes of Health. The government has certain rights in the invention.

TABLE OF CONTENTS

1. INTRODUCTION . . .
2. BACKGROUND OF THE INVENTION . . .
   2.1 IMMUNITY AND IMMUNIZATION . . .
   2.2 THE IMMUNE RESPONSE . . .
   2.3 ADOPTIVE IMMUNOTHERAPY OF CANCER . . .
3. SUMMARY OF THE INVENTION . . .
4. BRIEF DESCRIPTIONS OF DRAWINGS . . .
5. DETAILED DESCRIPTION OF THE INVENTION . . .
   5.1 SOURCES OF ANTIGENIC CELLS . . .
   5.2 SOURCES OF IMMUNE CELLS . . .
      5.2.1 IMMUNE CELLS PRIMED IN VIVO . . .
      5.2.2 IMMUNE CELLS PRIMED IN VITRO . . .
   5.3 GENERATION OF ANTIGEN-REACTIVE T CELLS . . .
   5.4 PREPARATIONS OF HEAT SHOCK PROTEIN-ANTIGEN COMPLEXES . . .
      5.4.1 PREPARATION AND PURIFICATION OF HSP 70 PEPTIDE COMPLEXES . . .
      5.4.2 PREPARATION AND PURIFICATION OF HSP 90 PEPTIDE COMPLEXES . . .
      5.4.3 PREPARATION AND PURIFICATION OF GP96 PEPTIDE COMPLEXES . . .
      5.4.4 IN VITRO PRODUCTION OF HSP-ANTIGENIC MOLECULE COMPLEXES . . .
   5.5 DETERMINATION OF REACTIVITY OF RESPONDING T CELLS . . .
   5.6 REINFUSION OF ANTIGEN-REACTIVE T CELLS . . .
   5.7 TARGET INFECTIOUS DISEASES . . .
   5.8 TARGET CANCERS . . .
6. EXAMPLES . . .
   6.1 MATERIALS . . .
   6.2 CHARACTERIZATION OF ANTIGEN-REACTIVE T CELLS
   6.3 ANTIGEN RECOGNITION BY CD4+ T CELLS . . .

1. INTRODUCTION

The present invention relates to methods for generating T cells reactive to an antigenic molecule (antigen-reactive T cells) for use in immunotherapy for the treatment and prevention of cancer and infectious diseases. The methods involve immunizing an animal and incubating the immune cells in vitro with a non-covalent complex of a heat shock protein (HSP) and an antigenic molecule. Methods for pulsing antigen presenting cells and/or immune cells with HSP-antigen complexes for the generation of CD4+ antigen-reactive T cells are provided. Methods and compositions are also provided for the treatment and prevention of cancer or infectious disease in a subject comprising administering to the subject antigen-reactive T cells that are expanded in vitro by the present methods.

2. BACKGROUND OF THE INVENTION

2.1 IMMUNITY AND IMMUNIZATION

The immune system protects a host against pathogens by mounting an immune response which is specific to an antigen of an invading pathogen. The objective of immunization is to elicit an early protective immune response by administering to the host an attenuated pathogen, or an antigen associated with a pathogen. This approach has been implemented successfully to prevent a variety of infectious diseases, such as polio, tetanus and diphtheria.

Immunization may be accomplished passively by administering either preformed immunoreactive serum or cells; or actively by presenting a suitable antigenic stimulus to the host's immune system.

Passive immunization is useful for a host who cannot produce antibodies, or for those who might develop disease before active immunization could stimulate antibody production. However, antibodies produced following some infections, particularly those due to mycobacteria, fungi, and many viruses, are not effective in protecting against the infection. Rather, the action of lymphocytes and macrophages largely determines recovery from these diseases.

Active immunization may be achieved with either viable or non-viable antigenic agents. Viable agents are generally preferred because the immune response provoked is more reliable and long-lived. However, viable vaccines may cause serious illness in an immunologically incompetent host, such as patients receiving corticosteroids, alkylating drugs, radiation or immunosuppressants. The use of attenuated strains always carries the risk that the attenuated agent may recombine with host DNA and mutate into a virulent strain. See generally, Ada, G. L., 1989, Chapter 36, in *Fundamental Immunology*, 2nd edition, ed. Paul W. E., Raven Press, New York, pp. 985–1032; Cohen, S. N., 1987, Chapter 37, in *Basic and Clinical Immunology*, 6th edition, ed. Stites, Stobo and Wells, Appleton and Lange, pp. 669–689.

2.2 THE IMMUNE RESPONSE

Cells of the immune system arise from pluripotent stem cells through two main lines of differentiation: a) the lymphoid lineage producing lymphocytes (T cells, B cells, natural killer cells), and b) the myeloid lineage (monocytes, macrophages and neutrophils, as well as accessory cells including dendritic cells, platelets and mast cells). In the circulatory system and secondary lymphoid organs of an adult animal, lymphocytes recirculate and search for invading foreign substances.

Pathogens and antigens tend to be trapped in secondary lymphoid organs, such as the spleen and the lymph nodes, where antigens are taken up or "captured" by antigen-presenting cells (APCs). The antigen presenting cells serve to display peptides and antigens to the immune cells by placing these peptides on the surface of the APC in association with a major histocompatibility complex (MHC) molecule. The process of antigen capture may occur by phagocytosis of exogenous proteins or by directed transport of proteins within the cell. Alternately, antigens may be derived from proteins synthesized within the cell. Next, antigens are processed into antigenic peptides by proteolytic degradation within the APC. The antigenic peptides are further complexed with a MHC molecule for presentation at the cell surface. Once an antigenic peptide is displayed by an MHC molecule on the antigen presenting cell (APC) surface, a cell-mediated immune reaction may follow which requires an interaction between the APC and a T cell. This interaction can trigger several effector pathways, including activation of T cells, and stimulation of T cell production of cytokines.

Interaction of an APC with a T cell is determined by several major components. These components include a) the T cell surface marker, b) the class of MHC molecule, and c) the T cell receptor (TCR).

T cells can be subdivided by their expression of surface markers CD4 and CD8. T cells expressing CD8 are often known as suppressor or cytotoxic cells. T cells expressing CD4 are often known as helper or inducer T cells. However, the CD8/CD4 dichotomy refers to the pattern of MHC association and antigen recognition. The CD8/CD4 nomenclature does not distinguish between cytotoxic and non-cytotoxic cells. The CD4 molecule binds to conserved structures of the class II MHC molecule. The CD8 molecule binds to conserved structures of class I MHC molecule.

The second factor important in APC/T cell interaction is the MHC. As indicated supra, the CD4 and CD8 molecules bind to the conserved structures of class II and class I MHC molecules, respectively. Class I and class II MHC molecules are the most polymorphic proteins known and play a major role in the immune system in the recognition of self and non-self. The heterogeneity of MHC molecule is observed at the level of haplotype or the combination of classes I and II MHC molecules encoded on a single chromosome. In the human, three distinct genetic loci designated, HLA-A, HLA-B and HLA-C, have been identified encoding class I molecules. Similarly, the three distinct loci encoding class II MHC molecules include HLA-DP, HLA-DR, and HLA-DQ. The multiple loci of MHC genes contribute to the complexity of self and non-self recognition process.

The third component important in APC/T cell interactions is the T-cell receptor (TCR). The TCR is responsible for the antigenic specificity of the T cell, and may only bind antigenic peptide that is associated with the polymorphic determinants of an MHC. Because the binding of the T-cell receptor is specific for a complex comprising an antigenic peptide and the polymorphic portion of the MHC molecule, T cells may not respond or respond poorly when an MHC molecule of a different genetic type is encountered. This specificity of binding results in the phenomenon of MHC-restricted T-cell recognition and T-cell cytotoxicity.

In pathogen-infected cells, proteins of the pathogens are degraded inside the cell. Some of the resulting peptides are transported into the lumen of the endoplasmic reticulum and may form complexes with class I MHC molecules. It has been previously shown that the pathogenic antigens can be chaperoned by heat shock proteins into the endogenous pathway whereby antigenic peptides become associated with the MHC molecules (Suto et al., 1995, Science 269:1585–1588; Srivastava et al., 1994, Immunogenetics 39:93–98). These peptide-MHC complexes are then transported to and accumulate on the cell surfaces, where they are recognized by receptors on T cells (Yewdell et al., 1992, Adv. Immunol. 52:1–123; Bevan, 1995, J. Exp. Med. 182:639–641).

T lymphocytes (T cells) are the critical regulatory and effector cells of the adaptive immune system. T lymphocytes develop and undergo selection in the thymus, and then mature into functional T cells in the tissues after receiving a series of signals. Early signals are triggered by specific antigen-MHC complexes on the surface of antigen-presenting cells (APC). The later signals may be provided by cytokines produced by CD4+ helper T cells, such as interferon-γ, and interleukin-2 (IL-2), interleukin-4 (IL-4), interleukin-7 (IL-7) and interleukin-12 (IL-12).

2.3 ADOPTIVE IMMUNOTHERAPY OF CANCER

Studies with experimental animal tumors as well as spontaneous human tumors have demonstrated that many tumors do express antigens that can induce an immune response. Some antigens are unique to the tumor, and some are found on both tumor and normal cells. Several factors can greatly influence the immunogenicity of the tumor induced, including, for example, the specific type of carcinogen involved, and immunocompetence of the host and latency period (Old et al., 1962, Ann. N.Y. Acad. Sci. 101:80–106; Bartlett, 1972, J Natl Cancer Inst 49:493–504). It has been demonstrated that T cell-mediated immunity is of critical importance for rejection of virally and chemically induced tumors (Klein et al., 1960, Cancer Res. 20:1561–1572; Tevethia et al., 1974, J. Immunol. 13:1417–1423). The cytotoxic T cell response is the most important host response for the control of growth of antigenic tumor cells (Anichimi et al., 1987, Immunol. Today 8:385–389).

Adoptive immunotherapy of cancer takes the therapeutic approach, wherein immune cells with an antitumor reactivity are administered to a tumor-bearing host, with the objective that the immune cells cause either directly or indirectly, the regression of an established tumor. Immunization of hosts bearing established tumors with tumor cells or tumor antigens has generally been ineffective since the tumor is likely to have elicited an immunosuppressive response (Greenberg, P. D., 1987, Chapter 14, in *Basic and Clinical Immunology*, 6th ed., ed. by Stites, Stobo and Wells, Appleton and Lange, pp. 186–196). Thus, prior to immunotherapy, it has been necessary to reduce the tumor mass and deplete all the T cells in the tumor-bearing host (Greenberg et al., 1983, page 301–335, in "Basic and Clinical Tumor Immunology", ed. Herbermann RR, Martinus Nijhoff).

Animal models have been developed in which hosts bearing advanced tumors can be treated by the transfer of tumor-specific syngeneic T cells (Mulé et al., 1984, Science 225:1487–1489). Investigators at the National Cancer Institute (NCI) have used autologous reinfusion of peripheral blood lymphocytes or tumor-infiltrating lymphocytes (TIL), T cell cultures from biopsies of subcutaneous lymph nodules, to treat several human cancers (Rosenberg, S. A., U.S. Pat. No. 4,690,914, issued Sep. 1, 1987; Rosenberg et al., 1988, N. Engl. J. Med., 319:1676–1680). For example, TIL expanded in vitro in the presence of IL-2 have been adoptively transferred to cancer patients, resulting in tumor regression in select patients with metastatic melanoma. Melanoma TIL grown in IL-2 have been identified as activated T lymphocytes CD3+ HLA-DR+, which are predominantly CD8+ cells with unique in vitro antitumor properties. Many long-term melanoma TIL cultures lyse autologous tumors in a specific class I MHC molecule and T cell antigen receptor-dependent manner (Topalian et al., 1989, J. Immunol. 142:3714).

Application of these methods for treatment of human cancers would entail isolating a specific set of tumor-reactive lymphocytes present in a patient, expanding these cells to large numbers in vitro, and then putting these cells back into the host by multiple infusions. However, the methods of Rosenberg for generating tumor-reactive lymphocytes require the use of intact irradiated tumor cells with potential broad antigen specificity, as a source of stimulation of lymphocytes. Additionally, since T cells expanded in the presence of IL-2 are dependent upon IL-2 for survival, infusion of IL-2 after cell transfer prolongs the survival and augments the therapeutic efficacy of cultured T cells (Rosenberg et al., 1987, N. Engl. J. Med. 316:889–897). However, the toxicity of the high-dose IL-2 and activated lymphocyte treatment has been considerable, including high fevers, hypotension, damage to the endothelial walls due to capillary leak syndrome, and various adverse cardiac events such as arrhythmias and myocardial infarction (Rosenberg et al., 1988, N. Engl. J. Med. 319:1676–1680). Furthermore, the demanding technical expertise required to generate TILs, the quantity of material needed, and the severe adverse side effects limit the use of these techniques to specialized treatment centers.

Despite the teachings of Rosenberg, severe deficiencies exist in the art regarding methods of cellular immunotherapy. In many instances, it is not possible to generate tumor cell line. Thus, it would be desirable to have a method for generating a large number of activated/stimulated T cells reactive to any antigen or a large repertoire of antigens without reliance on intact tumor cells, which would have the convenience of in vitro culture.

The process of T cell priming is poorly understood for most purposes. There have been occasional reports of priming of antigen-specific T cells in vitro (Steel and Nutman, 1998, J. Immunol. 160: 351–360; Tao et al., 1997, J. Immunol. 158:4237–44; Dozmorov and Miller, 1997, Cell Immunol. 178:187–96; De Bruijn et al., 1991, Eur J Immunol. 21:2963–2970; De Bruijn et al., 1992, Eur J Immunol. 22:3013–3020; Houbiers et al., 1993, Eur J Immunol. 26:2072–2077; Nair et al., 1997, Eur J Immunol. 27:589–597), however, they are restricted to instances where a higher expression of a given type of MHC I-peptide complex De Bruijn et al., 1991, Eur J Immunol. 21:2963–2970; Nair et al., 1997, Eur J Immunol. 27:589–597) or a particularly high avidity for the MHC I-peptide-T cell receptor interaction has been achieved (De Bruijn et al., 1991, Eur J Immunol. 21:2963–2970).

3. SUMMARY OF THE INVENTION

The present invention relates to methods for generating antigen-reactive T cells in vitro that can be used for the prevention or treatment of a disease or disorder, such as infectious disease or cancer. In one embodiment, the present invention relates to methods for generating antigen-reactive CD4+ T cells that can be used for the prevention or treatment of a disease or disorder, such as infectious disease and cancer. The methods of the invention provide CD4+ T cells that are capable of specifically killing or targeting antigenic cells, such as cancer cells or infected cells comprising an antigen with which the T cell has been stimulated.

The invention provides methods for generating T cells reactive to an antigen comprising immunizing an animal and incubating the immune cells in vitro with a non-covalent complex of heat shock protein and an antigenic molecule. In various embodiments, the invention provides immune cells used in the methods of the invention that are enriched for CD4+ T cells or antigen presenting cells.

Alternatively, in another embodiment immune cells that are primed/immunized in vitro can also be used. In various embodiments, antigenic cells are used as a source of antigenic molecule and/or HSP-antigen complex by the methods of the invention. The antigenic cells can be cancer cells or cells infected with a bacteria, fungus, parasite, or a protozoan. The invention further provides for the use of antigenic cells which expresses recombinant antigenic molecule or which have been infected in vitro with a pathogen or which have been transformed in vitro.

The invention provides the use of HSP-antigen complexes comprising a heat shock protein which is non-covalently complexed to an antigenic molecule. Specifically, the invention provides for the use of HSP60, HSP70, HSP90, HSP100, gp96 or a member of the small heat shock protein (HSP) family.

Methods are provided for stimulating and/or restimulating immune cells with a non-covalent complex of an HSP and an antigenic molecule. In one embodiment, the immune cell stimulation and/or restimulation result in antigen-reactive CD4+ T cells.

The invention provides methods of recovering antigen-reactive T cells from culture.

Further, the invention provides methods of treating or preventing a disease or disorder in a subject comprising generating T cells reactive to an antigenic molecule by a method of the invention and administering an effective amount of the antigen-reactive T cells to the subject. In a preferred embodiment, the T cells and antigenic cells have at least one MHC allele in common. In a more preferred embodiment, the T cells and the antigenic cells have more than one MHC allele in common. In most preferred embodiment, the method of the invention uses immune cells and antigenic cells from the same human.

4. BRIEF DESCRIPTIONS OF DRAWINGS

FIG. 1, FACS analysis using CD4 antibody and CD8 antibody of immune cells following stimulation and restimulation with Meth A cell lysate. The X and Y axes represent respectively the Fluorescent signal strength corresponding to the amount of CD8 and CD4 on the cell.

Figure 2:
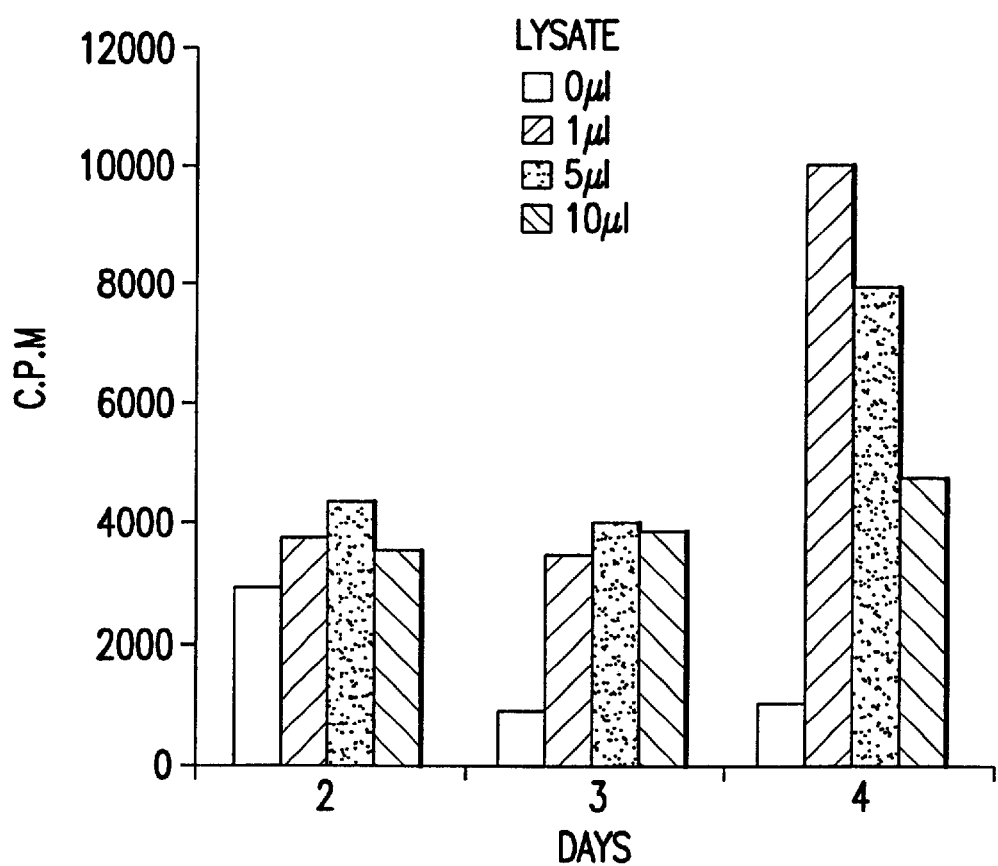

FIG. 2, Time course of proliferation response of immune cells treated with Meth A cell lysate as measured by incorporation of $^3$H-thymidine (counts per minute, c.p.m.).

Figure 3:
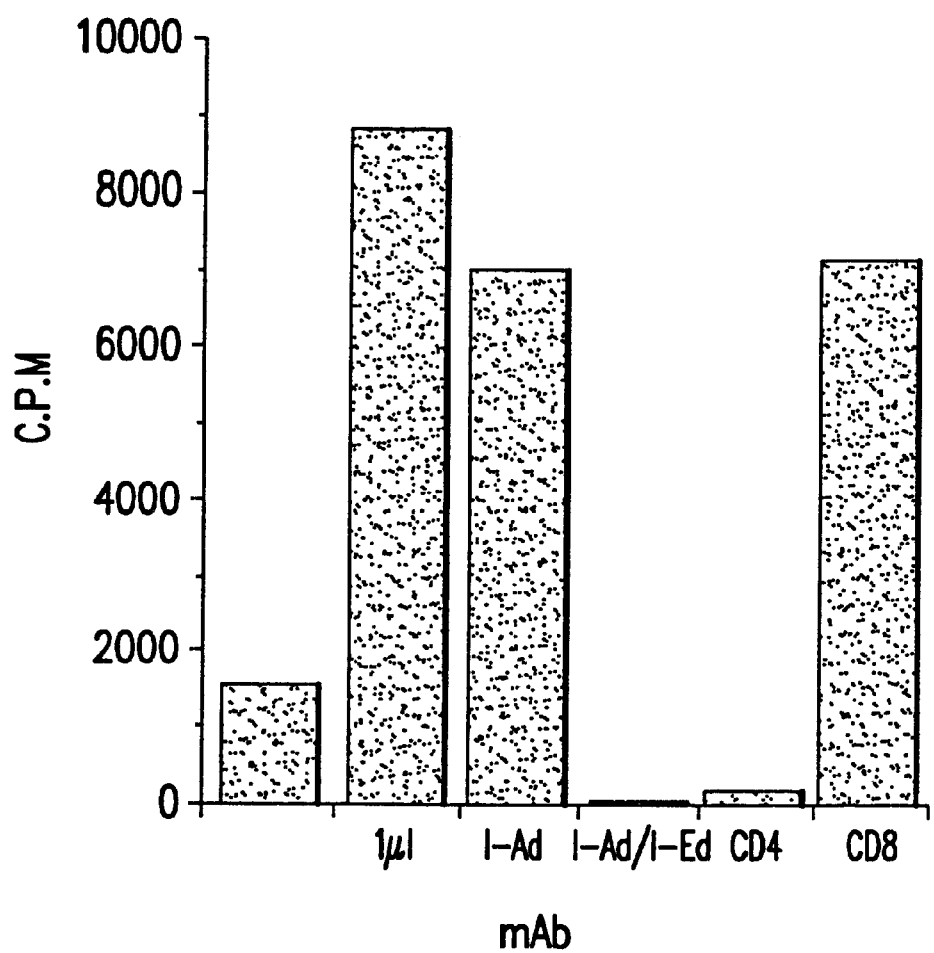

FIG. 3, Inhibition of proliferation response by incubation of monoclonal antibodies with in vitro cultured cells.

Figure 4:
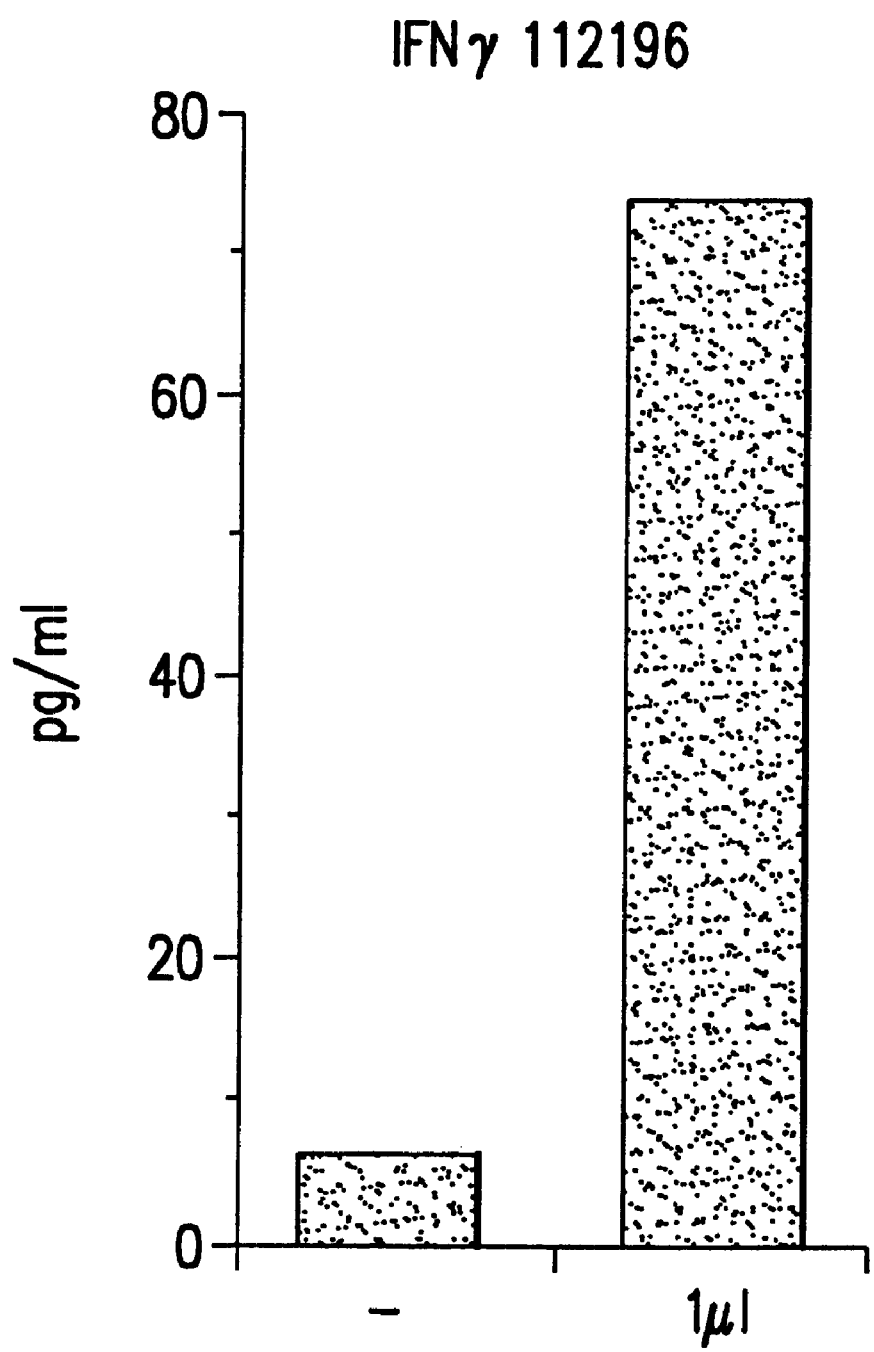

FIG. 4, Interron-gamma (IFnγ) secretion of T cells in the absence or presence of Meth A lysate.

Figure 5:
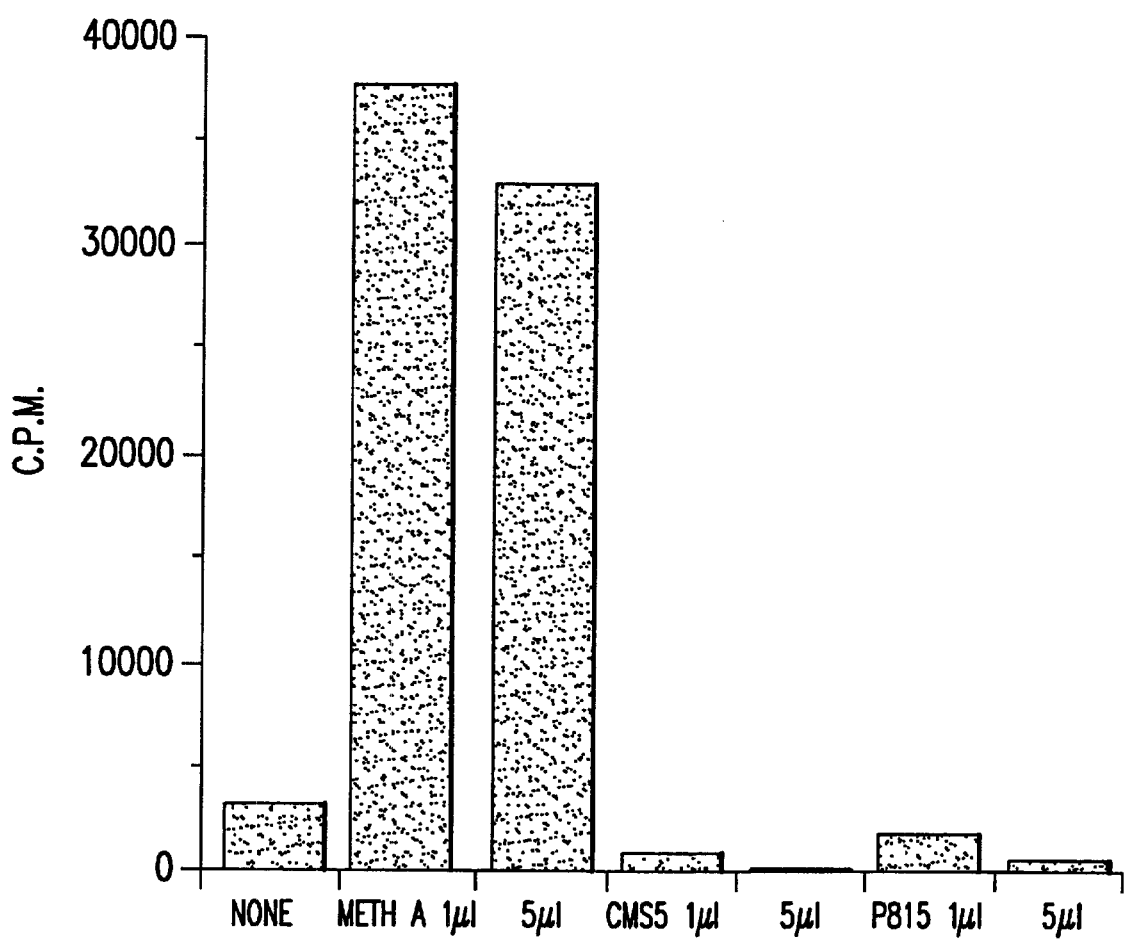

FIG. 5, Proliferation response of immune cells incubated with lysates from Meth A cells, CMS5 cells, or P815 cells, as measured by $^3$H-thymidine incorporation (counts per minute, c.p.m.).

Figure 6:
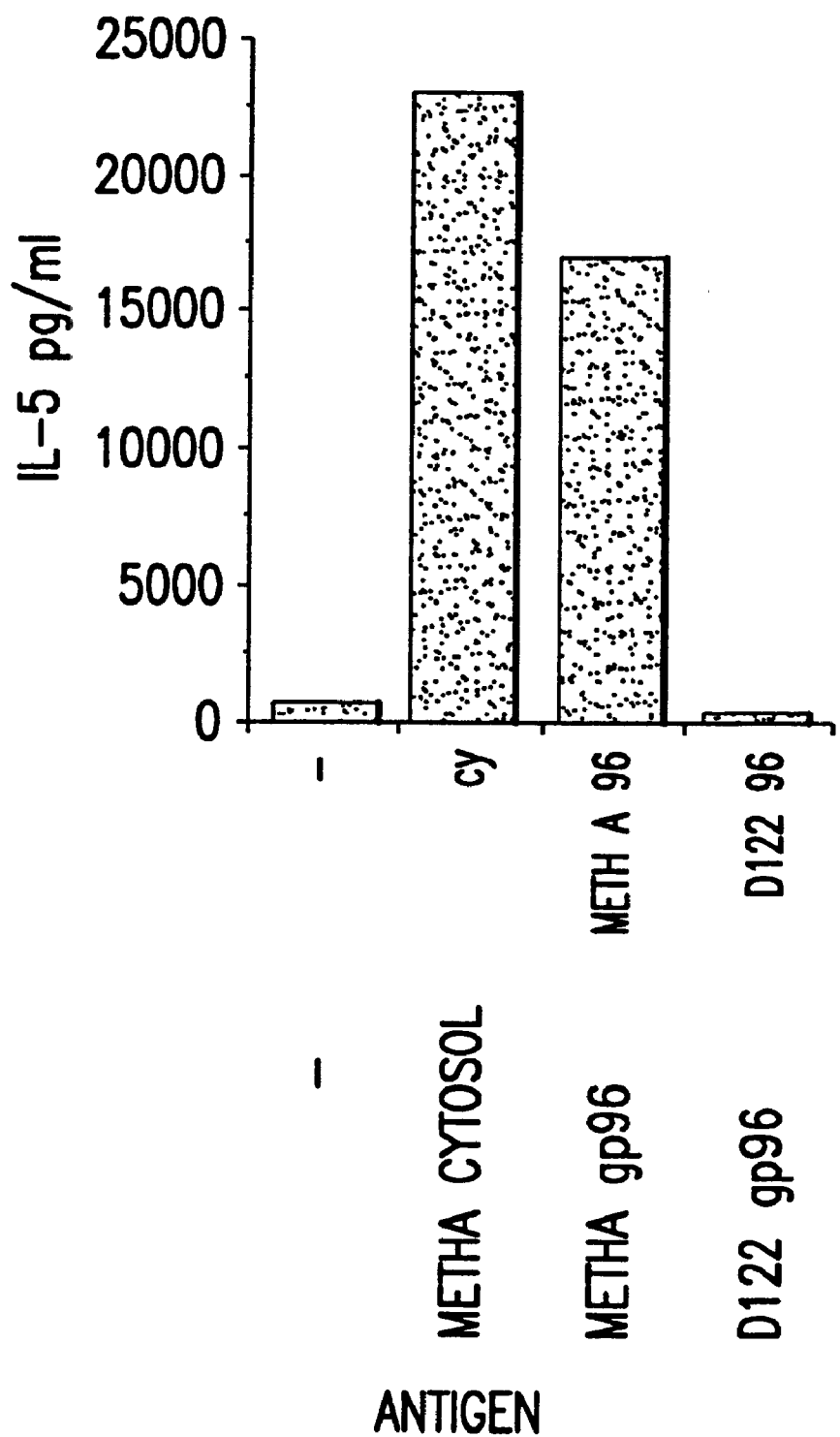

FIG. 6, Interleukin-5 (IL-5) secretion by T cells in response to gp96.

Figure 7:
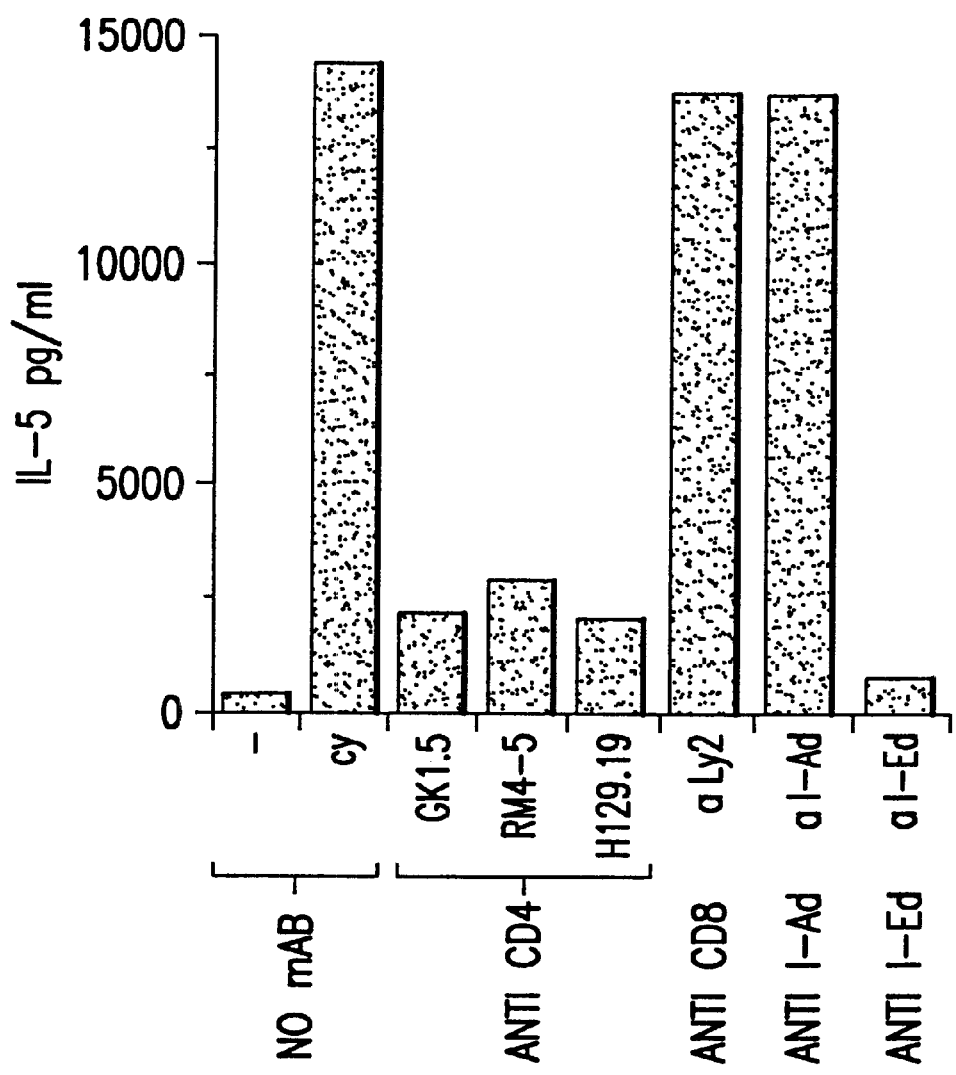

FIG. 7, Inhibition of Interleukin-5 (IL-5) secretion by antigen-reactive T cells in response to Meth A cell lysate by monoclonal antibodies to CD4, CD8, I-Ad, and IEd.

Figure 8:
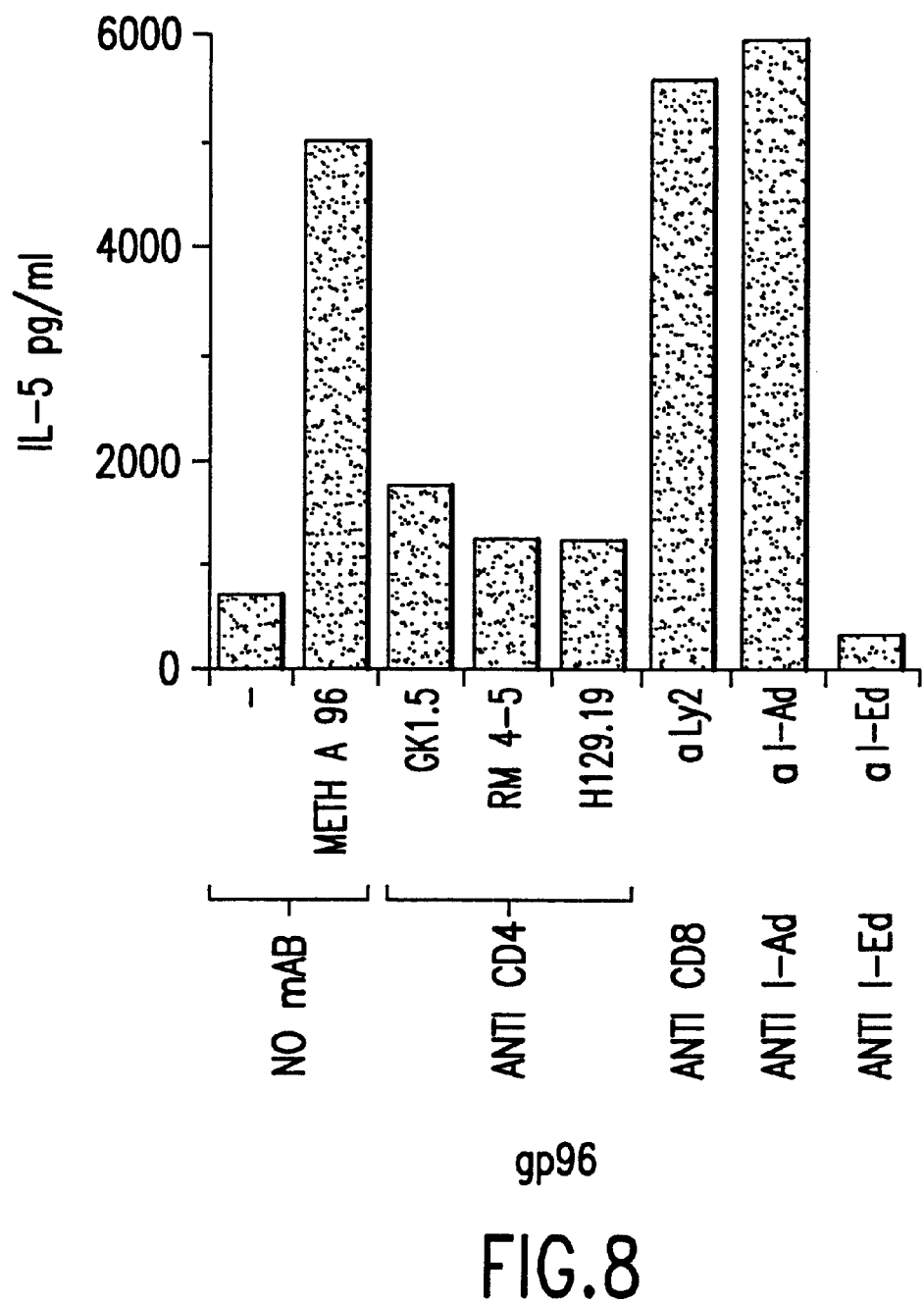

FIG. 8, Inhibition of Interleukin-5 (IL-5) secretion by antigen-reactive T cells in response to gp96 by incubation monoclonal antibodies to in vitro cultured cells.

Figure 9:
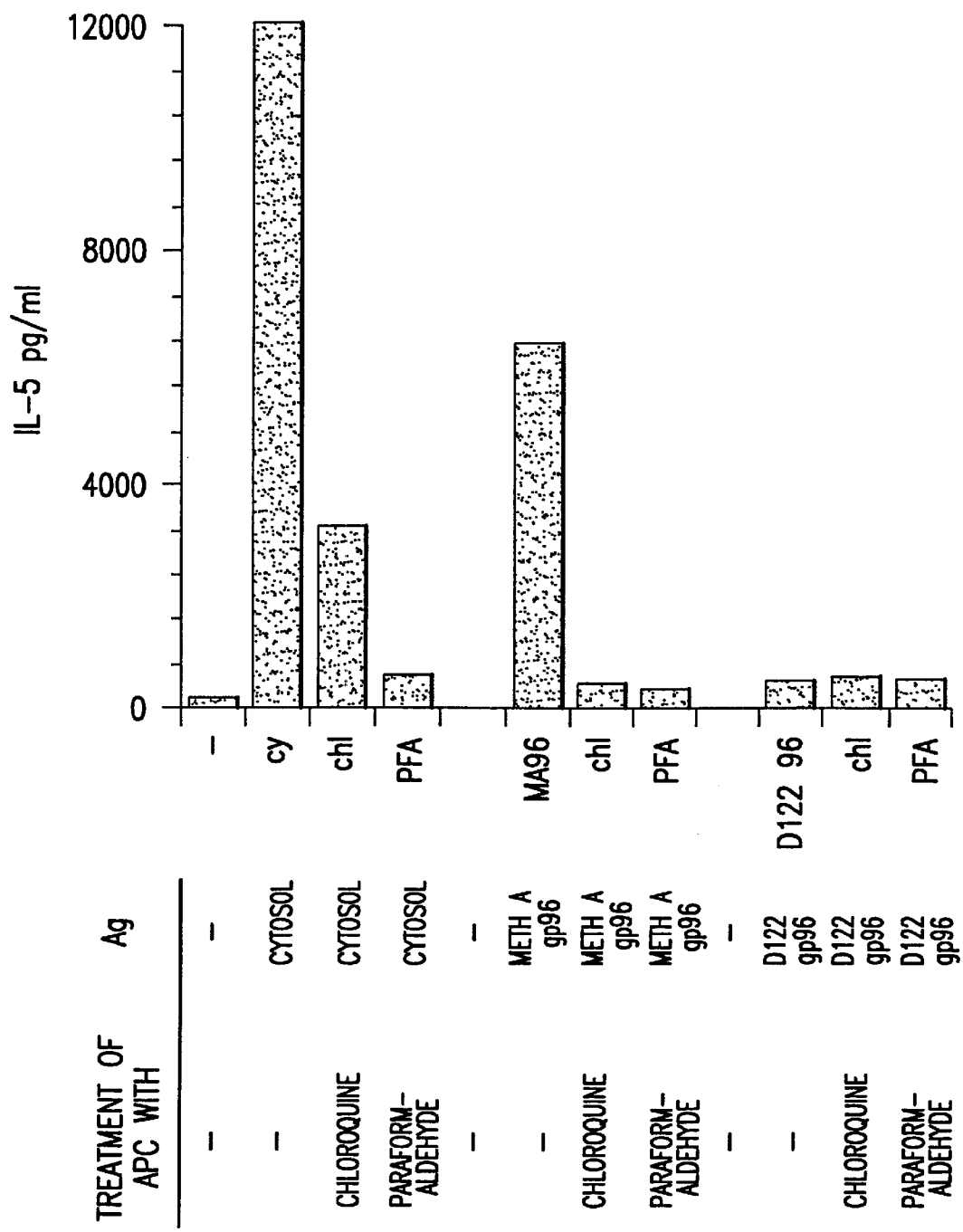

FIG. 9, Interleukin-5 (IL-5) secretion by antigen-reactive T cells generated by antigen presenting cells treated with Chloroquine or Paraformaldehyde.

Figure 10:
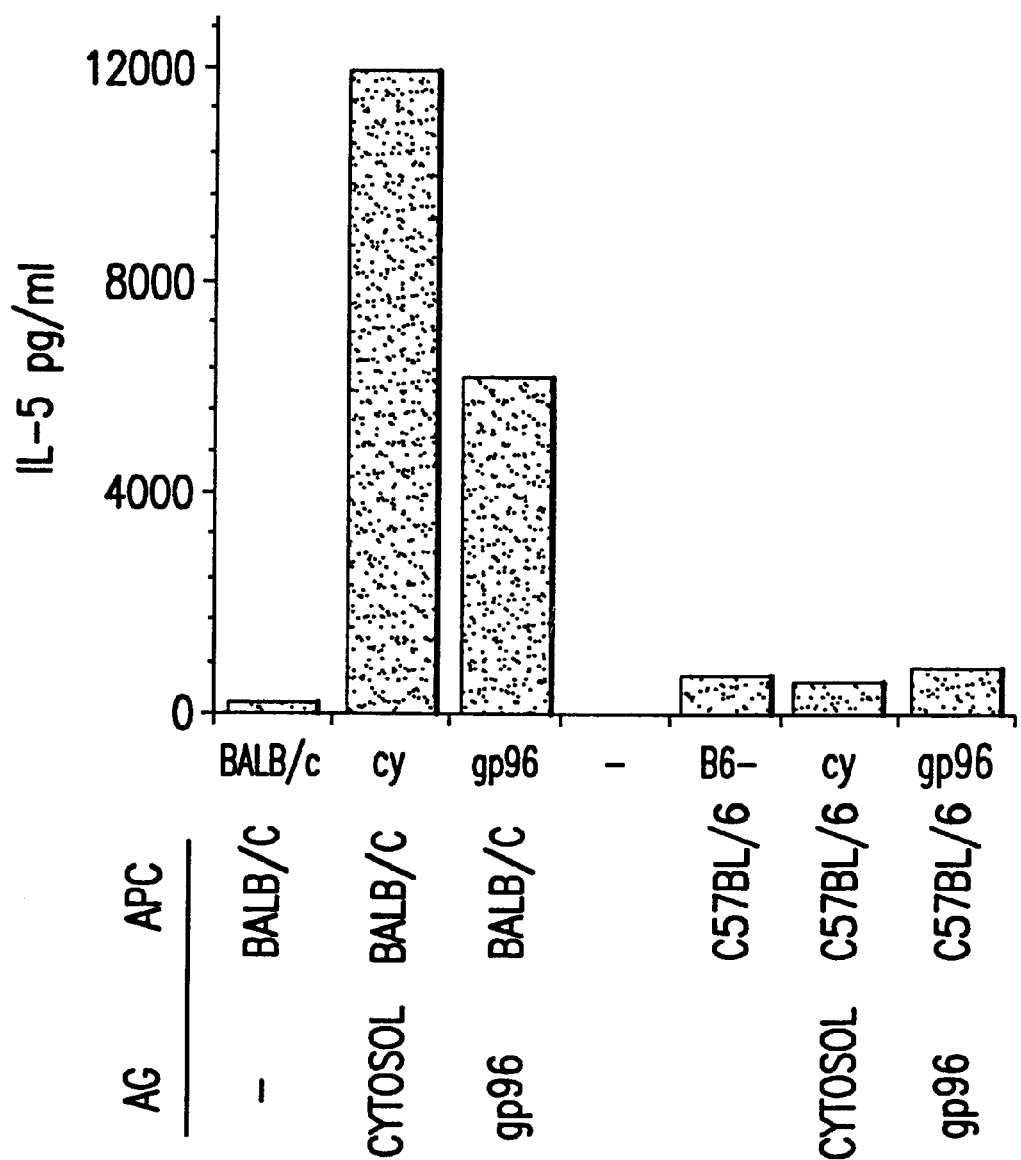

FIG. 10, MHC restrictions of the immune cell proliferation response.

5. DETAILED DESCRIPTION OF THE INVENTION

Antigen-reactive T cells are antigen-specific effector cells that are important in resisting pathogens, cancer and allograft rejection. Antigen-reactive T cells which are CD8+, recognize antigen presented by class I MHC molecules.

Class I MHC molecules are expressed by almost all cell types. Antigen-reactive T cells which are CD4+, recognize antigen presented by class II MHC molecules. Class II MHC molecules are expressed in a variety of cell types including dendritic cells, endothelial cells, monocytes, macrophages, and lymphocytes. The ability of antigen-reactive T cells to kill target cells is restricted by antigenic and genetic factors. For lysis of target cells, the target cells must carry the same antigen that originally induced the stimulation of the T cells, and the same class MHC molecule as the T cells.

The present invention relates to methods for generating T cells reactive to an antigen (herein synonymous with "antigen-reactive T cells") that can be used in the prevention or treatment of a disease or disorder, such as infectious disease and cancer. The inventor of the present invention discovered a method for expanding T cells reactive to an antigenic molecule, in vitro, by incubating immune cells, comprising T cells and antigen presenting cells with a substantially purified non-covalent complex of heat shock protein and an antigenic molecule. This invention was made possible by the surprising discovery that heat shock proteins can form non-covalent complexes with CD4+ T cell epitopes.

In one embodiment, the immune cells are obtained from an animal immunized with a molecule displaying the antigenicity of said antigenic molecule, whereby T cells reactive to the antigenic molecule are generated. In a specific embodiment, the T cells reactive to an antigenic molecule are generated by (a) immunizing an animal with an antigenic molecule; (b) obtaining a composition comprising immune cells from the animal, said immune cells comprising T cells and antigen presenting cells; and (c) incubating the immune cells in vitro with a substantially purified non-covalent complex of a heat shock protein and a molecule displaying the antigenicity of said antigenic molecule, whereby T cells reactive to the antigenic molecule are generated.

In an example of one embodiment, T cells reactive to an antigenic molecule are generated by a) priming immune cells in vivo, b) pulsing antigen presenting cells (APCs) with HSP-antigen complex in vitro, and c) co-culturing APCs with CD4+ T cells. These methods lead to the stimulation, proliferation and maturation of a specific set of antigen-reactive T cells, specifically CD4+ antigen-reactive T cells.

Further, HSP-antigen complex and APCs may be added multiple times to the in vitro cultures in order to restimulate antigen-reactive T-cell proliferation. The antigen-reactive T cells generated by the methods of the invention are capable of specifically targeting, killing, or causing lysis of the cancer cells, infected cells, or other target cells as the case may be, or any cells bearing the same antigens and similar MHC molecules with which the T cells are prepared. The antigen-reactive T cells of the invention may also secrete one or more cytokines, such as IL-2, IFN-γ, TNF-β, IL-4, IL-5, IL-6, IL-9, IL-9, IL-10, IL-3, or GM-CSF.

The antigen-reactive T cells can be administered in vivo autologously (i.e., to the same individual from which the T cells (or parental cells to the T cells) were originally obtained) or sygeneically (i.e., to an identical twin of the individual from which the cancer or infected cells were initially obtained); or allogeneically to an individual who shares at least one common MHC allele with the individual from which the antigenic cells and T cells were originally obtained.

As used herein, the term "antigenic cells" refers to any cells, preferably cancer cells or infected cells, which can elicit an immune response in a subject. The sources of antigenic cells, and methods of preparation of antigenic cells for use in the present methods are discussed in section 5.1.

As used herein, "immune cells" are a mixture of cells comprising T cells and antigen presenting cells. The antigen presenting cells include but are not limited to macrophages, dendritic cells, and/or B cells.

The term "priming" as used herein includes the process of immunization in vivo, as well as the process of immunization in vitro. The process of immunization in vivo includes, but is not limited to immunizing a live animal with a) the same heat shock protein (HSP) preparation that is subsequently used for in vitro stimulation of APCs or primed immune cells, b) irradiated antigenic cells, and c) a lysate or extract of an antigenic cell. The process of immunization in vitro may be performed by a variety of methods including but not limited to the dendritic cells pulsed with antigens (Steel and Nutman, 1998, J. Immunol. 160: 351–360; Tao et al., 1997, J. Immunol. 158:4237–44; Dozmorov and Miller, 1997, Cell Immunol. 178:187–96; Inaba et al., 1987; J Exp Med. 166:182–194; Macatonia et al., 1989; J Exp Med. 169:1255–1264; De Bruijn et al., 1992, Eur J Immunol. 22:3013–3020), RMA-S cells (mutant cells expressing high numbers of 'empty' cell surface class I MHC molecules) loaded with peptide (De Bruijn et al., 1991, Eur J Immunol. 21:2963–2970; De Bruijn et al., 1992, Eur J Immunol. 22:3013–3020; Houbiers et al., 1993, Eur J Immunol. 26:2072–2077) and macrophage phagocytosed-peptide loaded beads (De Bruijn et al., 1995, Eur J Immunol. 25:1274–1285), and osmotically stressed antigenic cells (PCT publication WO 98/15616). Priming, therefore, results in the first exposure of naive immune cells to an antigenic molecule.

The term "pulsing" as used herein refers to the process of exposing primed immune cells in vitro to HSP-antigen complex. An "HSP-antigen complex", as used herein, comprises a non-covalent complex of a heat shock protein and an antigenic molecule. Sources of HSP-antigen complex include but are not limited to HSP preparations. Such preparations include a purified non-covalent complex of an HSP and an antigenic molecule (as described in section 5.4 infra), an HSP-antigen complex present in a cell lysate or extract, a complex formed in vitro of HSP and an antigenic molecule. In a specific embodiment, the HSP-antigen complex is a substantially purified preparation. In another specific embodiment, the HSP is HSP60, HSP70, HSP90, HSP100, gp96 or a member of the small heat shock protein (sHSP) family (Kim et al., 1998, Nature 394:595–599). In another embodiment of the invention, APCs are exposed to an HSP-antigen complex by the addition of a non-covalent complex of an HSP and antigenic molecule to in vitro cultured APCs.

According to the invention, cellular immunotherapy is carried out by obtaining antigenic cells and immune cells from one or more, preferably the same subject, and stimulating T cells within the immune cell population by the methods of the invention. This in vitro stimulation of T cells, followed by clonal expansion in cell culture of antigen-reactive CD4+ or CD8+ T cells, and administration of the antigen-reactive T cells into the subject, constitute a useful therapeutic and prophylactic strategy. When infused into the subject, antigen-reactive T cells of the invention can specifically target and/or directly kill target cells in vivo that bear the same antigen as the antigenic cells, thereby inhibiting cancer growth, or preventing or limiting the spread of the pathogen in the recipient.

In a preferred embodiment of the invention, the antigenic cells, and the T cells, and the recipient of the antigen-reactive T cells have the same MHC haplotype. In a preferred embodiment, the invention is directed to the use of autologous T cells stimulated in vitro with autologously-derived antigen for the treatment or prevention of cancer or infectious disease in the same subject from which the T cells (or preferably, all the immune cells) and antigen were originally derived. In a more preferred aspect, the immune cells and antigenic cells are isolated from a human subject in need of cellular immunotherapy.

In another embodiment of the invention, the T cells and the recipient have the same haplotype while the antigenic cells are allogeneic to the T cells and the recipient but matched at least one MHC allele, i.e., antigenic cells are used to activate T cells, which T cells are then administered to a recipient from which the T cells were originally obtained, and in which the antigenic cells and the T cells share at least one but not all MHC alleles.

In a least preferred embodiment of the invention, the antigenic cells, the T cells and the recipient are all allogeneic with respect to each other, but all have at least one common MHC allele shared among the antigenic cells, the T cells and the recipient.

According to the invention, the methods for generating antigen-reactive T lymphocytes comprise priming live immune cells, pulsing the primed immune cells comprising APCs with HSP-antigen complex in vitro, and co-culturing the pulsed cells with primed T cells. In one embodiment, the primed immune cells are enriched for APCs prior to pulsing. In another embodiment, the primed immune cells are separated to generate enriched or purified populations of T cells or APCs. In a specific embodiment, primed immune cells are separated to generate enriched or purified populations of CD4+ T cells prior to pulsing. Co-culturing of pulsed cells with T cells lead to the stimulation of specific T cells which mature into antigen-reactive CD4+ T cells or antigen-reactive CD8+ T cells respectively.

Without limitation of the present invention to any particular scientific model or mechanism, the results described herein suggest that pulsed immune cells comprising APCs are uniquely enabled to induce antigen-specific activation of CD4+ T cells in vitro.

In another embodiment of the invention, the methods may further comprise restimulation of the antigen reactive T cells in vitro, by culturing the cells with feeder cells and irradiated antigenic cells, optionally in the presence of a composition comprising one or more cytokines (e.g., purified IL-2, Con A-stimulated spleen cell supernatant). In vitro restimulation of T cells by addition of APC and/or HSP-antigen to the culture may be used to promote expansion of the T cell populations.

In yet another embodiment, the T cells are stimulated with irradiated spleen cells or APCs purified from peripheral blood as feeder cells in the presence of HSP-antigen complex. In this manner, by restimulation from time-to-time, a stable antigen-specific T cell culture or cell line can be maintained in vitro for long periods of time. The T cell culture or cell line thus created can be stored, and if preserved (e.g., by formulation with a cryopreservative and freezing) used to resupply antigen-reactive T cells at desired intervals for long term uses.

In yet another embodiment of the invention, the effectiveness of the in vitro pulsing reaction can be enhanced by inclusion in the in vitro pulsing reaction of non-covalent complexes of heat shock protein and antigenic molecules. The complexes may be recovered from the antigenic cells, or prepared in vitro in which the peptide has the antigenicity of an antigen of interest of the antigenic cells. In one embodiment, the preparation of HSP-antigen complex is substantially purified. In another embodiment, the preparation comprises about 70%, 80%, 90% or 95% HSP-antigen complex.

According to a specific embodiment of the invention, antigen-reactive CD4+ T cells can be generated and used prophylactically to prevent infection, or development or remission of cancer. Antigen-reactive CD8+ T cells can also be generated and used prophylactically to prevent infection, or development or remission of cancer. In another embodiment, such T cells can be used therapeutically to treat infection or its sequelae, or to treat cancer. Preferably, the antigenic cells used to generate the antigen-reactive T cells are syngeneic to the subject to which they are to be administered, e.g., are obtained from the subject. However, if cancer cells or pathogen-infected cells that are syngeneic to the subject are not available for use, the methods of the invention provide that such antigenic cells having the same MHC haplotype as the intended recipient of the cells can be prepared in vitro using noncancerous or uninfected cells (e.g., normal cells) collected from the recipient. For example, depending on the mode of transmission of the pathogen, normal cells obtained from the recipient can be infected in vitro by incubation with the pathogen or other pathogen-infected cells, and then used to prime the host immune cells in vivo. In another embodiment lysates or preparations of cells infected with a pathogen in vitro, or thereof, can be used to pulse APCs or primed immune cells comprising APCs in vitro. In still another embodiment, lysates or preparations of cells infected with a pathogen in vitro, can be used for restimulation of antigen-reactive T cells of the invention.

In another embodiment, normal cells can be induced to become cancerous or transformed, e.g., by treatment with carcinogens, such as chemicals and/or radiation or infection with a transforming virus, and then used for priming directly or used to prepare lysate or HSP-antigen complexes for priming. In another embodiment, lysates or preparations of such cancerous, transformed, or infected cells can be used to pulse immune cells or APCs in vitro. In still another embodiment, the lysates or preparations of such cells, can be used for restimulation of the antigen-reactive T cells of the invention.

Furthermore, in another embodiment, if the cloned gene of the antigen of interest is available, normal cells from the subject can be transformed or transfected with the gene, such that the antigen of interest is expressed recombinantly in the cells, and then such cells can be used in the priming, pulsing, and/or restimulation reactions. In a less preferred aspect, antigenic cells for use can be prepared from cells that are not syngeneic but that have at least one MHC allele in common with the intended recipient.

In an immune response, the process of antigen-induced T cell activation occurs in vivo typically in secondary lymphoid tissues, such as the lymph nodes and the spleen. By following the present methods, any antigenic cells of interest can be used to prime T cells in vitro, even cancer cells or infected cells that are considered unsafe for use in active immunization. Such primed T cells are then exposed to APCs pulsed with HSP-antigen complex. In a specific embodiment CD4+ antigen-reactive T cells are expanded in vitro as a source of cells for immunotherapy. Thus, one advantage of the present methods is that antigen-specific T cells can be expanded in vitro to create a source of cells for immunotherapy that can be used for treatment or prevention of disease.

There are many advantages of immunotherapy as provided by the present invention. Tumor bulk is minimal following surgery and immunotherapy is most effective in this situation. In a specific embodiment, the preventive and therapeutic methods of the invention are directed at enhancing the immunocompetence of a cancer patient either before surgery or after surgery, and enhancing cell-mediated tumor-specific immunity against cancer cells, with the objective being inhibition of proliferation of cancer cells, and total eradication of residual cancer cells in the body.

In another preferred aspect, antigen-reactive T cells reactive against human cancer cells can be used, alone or in conjunction with surgery, chemotherapy, radiation or other anti-cancer therapies, to eradicate metastases or micrometastases, or to purge bone marrow of cancer cells during bone marrow transplantation. For example, to eradicate or inhibit the growth of metastases or micrometastases, the antigen-reactive T cells provided by the invention, CD4+ T cells in particular, are administered in vivo, to the subject having or suspected of having the metastases or micrometastases. For example, to purge bone marrow of cancer cells during bone marrow transplantation, bone marrow from the donor is contacted in vitro with the antigen-reactive T cells provided by the invention, so that the antigen reactive T cells lyse any residual cancer cells in the bone marrow, prior to administering the bone marrow to the subject for purposes of hematopoietic reconstitution. The bone marrow transplantation is preferably autologous. In one embodiment, the antigen-reactive T cells are CD4+ T cells. Alternatively, administration of the antigen-reactive T cells involved both CD4+ T cells and CD8+ T cells.

Moreover, if cancer patients undergo surgery with anesthesia, and subsequent chemotherapy, the resulting immunosuppression experienced by the patient may be lessened by cellular immunotherapy in the preoperative period, thereby reducing the incidence of infectious complications. There is also the possibility that tumor cells are shed into circulation at surgery, and thus, effective immunotherapy applied at this time can eliminate these cells in vivo. The invention thus provides a method of prophylaxis or treatment comprising administering to a-cancer patient the antigen-reactive T cells provided by the present invention, reactive against an antigen of the patient's cancer cells, prior to, during, and/or subsequent to surgery and/or chemotherapy undergone by the cancer patient.

In a preferred aspect involving acute viral infection of humans, CD4+ T cells are reactive against virus-infected cells of a human subject and can be rapidly generated and reinfused back to the subject for controlling the viral infection.

In another preferred aspect, the invention provides CD4+ T cells reactive against an opportunistic pathogen that infects immunosuppressed or immunodeficient subjects, such as but not limited to cytomegalovirus, Toxoplasma gondii, Herpes zoster, Herpes simplex, Pneumocystis carinii, Mycobacterium avium-intracellulare, Mycobacterium tuberculosis, Cryptosporidium, and Candida species. The antigen-reactive T cells of the invention can be used therapeutically, and preferably autologously, in human patients suffering from acquired immunodeficiency syndrome (AIDS) and associated infections and cancers, or prophylactically in subjects that are infected with the human immunodeficiency virus (HIV), or HIV seropositive subjects or otherwise at high risk for developing AIDS.

5.1 SOURCES OF ANTIGENIC CELLS

In various embodiments of the invention, any cell can be used as long as the cell has a molecule displaying the antigenicity of the antigen to which specifically reactive T cells are desired. It is not essential to use cells of the ultimate target cells in vivo (e.g., of the tumor or infected cells of the intended recipient that it is desired to inhibit) to stimulate/restimulate the T cells, so long as the antigen(s) on the target cells is present on the cells used in priming the immune cells. However, since whole cancer cells or infected cells or other antigenic cells are used in the present methods, it is not necessary to isolate or characterize or even know the identities of these antigens in advance of using the present methods. The antigenic cells of the invention are a source of the HSP-antigen complexes used in the pulsing of APCs or immune cells comprising APCs, and the restimulation of antigen-reactive T cells. Methods of preparation of HSP-antigen complexes from antigenic cells are provided in Sections 5.4.1 to 5.4.3.

For treatment or prevention of cancer, the methods of the invention provide T cells reactive against an antigenic molecule present in the cancerous or tumor cells e.g., tumor-specific antigens and tumor associated antigens, such that the T cells will induce or enhance an immune response against the cancer cells or tumor, preferably human cancers. For treatment or prevention of infectious diseases, the methods of the invention provide CD4+ or CD8+ T cells reactive against antigenic molecules such that T cells will induce or enhance an immune response against host cells infected by the pathogen that causes the infectious disease or against the pathogen, including but not limited to, viruses, bacteria, fungi, protozoans, parasites, etc., and preferably pathogens that infect humans.

As described above, the immune cells used in priming, pulsing and/or stimulation/restimulation, the T cells, and the antigenic cell must have at least one common MHC allele in order for effective stimulation of T cells to occur. The more MHC alleles in common, the more preferred the method. The most preferred method is one in which the primed immune cells and antigenic cells are derived from the intended recipient (i.e., all are autologous). The less preferred method is one in which the T cells are autologous to the recipient, but the antigenic cells are nonautologous (but share at least one MHC allele with the T cells). The least preferred method is one in which neither the T cells or antigenic cells are autologous to the recipient, but the T cells, antigenic cells, and recipient all have at least one MHC allele in common.

If the antigenic cells, T cells and target cells are obtained from the same or syngeneic individual, such cells will all have the same MHC haplotype. If all are not obtained from the same subject, and it is-not known and it is desired to assess whether the primed immune cells, T cells, and/or target cells have the same MHC haplotype or any MHC alleles in common, such can be determined by standard HLA typing techniques well known in the art, such as serological tests and DNA analysis of the MHC loci. Such a determination of MHC haplotype need not be undertaken prior to carrying out the priming and pulsing methods of the invention; one may simply carry out such methods and the obtaining of the desired T cell proliferation activity indicates that the matching MHC alleles were present.

The source of the antigenic cells may be selected, depending on the nature of the disease with which the antigen is associated, and the intended use of the resulting antigen-reactive T cells. In one embodiment of the invention, any tissues, or cells isolated from a cancer, including cancer that has metastasized to multiple sites, can be used in the present method. For example, leukemic cells circulating in blood, lymph or other body fluids can also be used, solid tumor tissue (e.g., primary tissue from a biopsy) can be used. Examples of cancers that are amenable to the methods of the invention are listed infra.

In another embodiment of the invention, any cell that is infected with a pathogen, in particular, an intracellular pathogen, such as a virus, bacterium, fungus, parasite, or protozoan, can be used. An exemplary list of infectious diseases that can be treated or prevented by antigen-reactive T cells of the invention is provided below.

Cell lines derived from cancer tissues, cancer cells, or infected cells can also be used as antigenic cells, provided that the cells of the cell line have the same antigenic determinant(s) as the antigen of interest on the antigenic cells. Cancer or infected tissues, cells, or cell lines of human origin are preferred.

Cancer cells or infected cells can be identified and isolated by any method known in the art. For example, cancer cells or infected cells can be identified by morphology, enzyme assays, proliferation assays, or the presence of pathogens or cancer-causing viruses. If the characteristics of the antigen of interest are known, antigenic cells can also be identified or isolated by any biochemical or immunological methods known in the art. For example, cancer cells or infected cells can be isolated by surgery, endoscopy, other biopsy techniques, affinity chromatography, and fluorescence activated cell sorting (e.g., with fluorescently tagged antibody against an antigen expressed by the cells).

If the number of antigenic cells obtained from a subject is insufficient, the cells may be cultured in vitro by standard methods to expand the number of cells prior to use in the present methods. There is no requirement that a clonal or homogeneous or purified population of antigenic cells be used to prime the T cells. A mixture of cells can be used provided that a substantial number of cells in the mixture contain the antigen of interest. In a specific embodiment, the antigenic cells and/or immune cells are substantially purified. In another embodiment, the primed immune cells are separated to create enriched populations of APCs or CD4+ T cells to be used in the methods of the invention.

In another embodiment of the invention, antigen-reactive T cells are generated for prophylaxis against cancer or infectious disease. In this instance, the appropriate autologous antigenic cells may not exist, since the recipient of the antigen-reactive T cells may not have the cancer or the infectious disease. Moreover, in an embodiment wherein the T cells are used for prophylaxis, desired quantities of autologous antigenic cells may not be obtainable from the recipient. In such instances, a source of antigenic cells having at least one common MHC allele, or preferably the same MHC haplotype as the recipient, which is used to prime or stimulate the CD4+ T cells, can be prepared in vitro from noncancerous or uninfected cells (e.g., normal cells), as appropriate, obtained from the recipient or other individual sharing at least one MHC allele with the recipient.

In order to prepare suitable antigenic cells that are cancer cells, noncancerous cells, preferably of the same cell type as the cancer desired to be inhibited, can be isolated from the recipient or, less preferably, other individual who shares at least one MHC allele with the intended recipient. These normal cells may then be treated with agents that cause the particular or a similar cancer or a transformed state; such agents may include but not limited to, radiation, chemical carcinogens, oncogenes, and viruses. Standard techniques can be used to treat the cells and propagate the cancer or transformed cells so produced.

In order to prepare pathogen-infected cells, uninfected cells of a cell type susceptible to infection by the pathogen can be infected in vitro with the pathogen that causes the disease. Depending on the mode of transmission and the biology of the pathogen, standard techniques can be used to facilitate infection by the pathogen, and propagation of the infected cells. For example, influenza viruses may be used to infect normal human fibroblasts; and mycobacteria may be used to infect normal human Schwann cells.

Alternatively, if the gene encoding a tumor-specific antigen, tumor-associated antigen or antigen of the pathogen is available, normal cells of the appropriate cell type from the intended recipient or an individual having at least one common MHC allele may be transformed or transfected in vitro with an expression construct containing the gene such that the antigen is expressed in the recipient's cells. optionally, more than one such antigen may be expressed in the recipient's cell in this fashion, as will be appreciated by those skilled in the art, any techniques known, such as those described in Ausubel et al. (1989, Current Protocols in Molecular Biology, Wiley Interscience), may be used to perform the transformation or transfection and subsequent recombinant expression of the antigen gene in recipient's cells. These antigenic cells bearing one or more MHC molecules in common with the recipient are suitable for use in the priming, pulsing or restimulation reactions of the invention.

5.2 SOURCES OF IMMUNE CELLS

The immune cells used according to the present invention, comprise a mixture of living cells of lymphoid and myeloid lineages, wherein the lymphoid cells comprise T cells that can be activated to differentiate into CD4+ T cells and CD8+ T cells, and wherein the myeloid cells comprise antigen-presenting cells (e.g., macrophages) that are functional in antigen-induced T cell activation. Preferably, the T cells have the same MHC haplotype as the antigenic cells and the target cells in the recipient.

5.2.1 IMMUNE CELLS PRIMED IN VIVO

According to the invention, immune cells are primed in vivo, then removed from the host and cultured such that T cells reactive to an antigenic molecule can be expanded in vitro.

The in vivo priming reaction of the present invention can be carried out by one of several methods. One method for in vivo priming includes immunization of an animal or human recipient with a heat shock protein (HSP) preparation in which the preparation comprises one or more antigenic peptides of interest. In a specific embodiment, the antigenic peptide of interest is non-covalently complexed to the HSP. Preparation of the HSP-antigen complexes is described in Section 5.4. In a preferred aspect of the invention, in vivo priming reactions using HSP preparations are followed by pulsing reactions of antigen presenting cells with the same HSP preparation.

In an alternate method for in vivo priming reaction, immunization of the recipient is performed using lysates or extracts derived from antigenic cells. A preferred and exemplary, non-limiting protocol for carrying out the in vivo priming reaction is provided hereinbelow:

Approximately $6\times10^7$ cells/ml of cancer or infected cells are suspended in plain media and lysed by freeze and thaw five times. Portions of total cell lysate for use in immunization is emulsified in an equal volume of a suitable adjuvant. Over a period of time, the recipient is given multiple immunizations with the cell lysate preparation. Following a number of immunizations, the resulting "primed" immune cells are collected from recipient as described herein.

Alternately, immunizations may be carried out by standard methods know in the art. (See generally, *Current Protocols in Immunology*, 1997, R. Coico ed., Wiley & Sons, Inc., New York).

Immune cells can be collected or isolated from blood, or secondary lymphoid organs of the subject, such as but not limited to lymph nodes, tonsils, the spleen, Peyer's patch of the intestine, and bone marrow, by any of the methods known in the art. Immune cells obtained from such sources typically comprise predominantly recirculating lymphocytes and APCs such as macrophages at various stages of differentiation and maturation. Optionally, standard techniques, such as morphological observation and immunochemical staining, can be used, if desired, to verify the presence of the desired cells, e.g., T cells, and macrophages.

In a preferred aspect, the immune cells obtained from a live animal are human peripheral blood compositions lacking red blood cells, e.g., whole blood leukocytes (whole peripheral blood from which the red blood cells and serum have been substantially removed), which can be collected from a human subject by standard techniques, such as by use of a syringe to withdraw the blood, followed by'subjecting the blood to Ficoll-Hypaque (Pharmacia) gradient centrifugation. Blood, anticoagulated with preservative-free heparin, usually yields 0.5 to $1 \times 10^6$ lymphocytes/ml. Separated blood cells (e.g., leukocytes) may be frozen by standard techniques prior to use in the present methods. In a specific embodiment, the immune cells used are purified white blood cells comprising lymphocytes and macrophages.

T cells and antigen presenting cells, such as macrophages, can be obtained together, or separately (and then combined for use in the stimulation/restimulation reaction), or optionally purified by any of various methods known in the art. In a preferred aspect of the invention, APCs, CD4+ T cells, and CD8+ T cells are purified or enriched prior to co-culturing of APCs with T cells resulting in the stimulation of the antigen-reactive T cells. In an example of one aspect of the invention human macrophages obtained from human blood cells are used as APCs. By way of example but not limitation, macrophages can be obtained as follows:

Mononuclear cells are isolated from peripheral blood of a patient (preferably the patient to be treated), by syringe removal of blood followed by Ficoll-Hypaque gradient centrifugation. Tissue culture dishes are pre-coated with the patient's own serum or with AB+ human serum and incubated at 37° C. for 1 hr. Non-adherent cells are removed by pipetting. To the adherent cells left in the dish, is added cold (4° C.) 1 mM EDTA in phosphate-buffered saline and the dishes are left at room temperature for 15 minutes. The cells are harvested, washed with RPMI buffer and suspended in RPMI buffer. Increased numbers of macrophages may be obtained by incubating at 37° C. with macrophage-colony. stimulating factor (M-CSF).

5.2.2 IMMUNE CELLS PRIMED IN VITRO

Priming of immune cells in vitro may be accomplished by several methods including but not limited to the use of dendritic cells (DCs) pulsed with appropriate antigens (Inaba et al., 1987; J Exp Med. 166:182–194; Macatonia et al., 1989; J Exp Med. 169:1255–1264; De Bruijn et al., 1992, Eur J Immunol. 22:3013–3020;, RMA-S cells (mutant cells expressing high numbers of 'empty' cell surface class I MHC molecules) loaded with peptide (De Bruijn et al., 1991, Eur J Immunol. 21:2963–2970; Steel and Nutman, 1998, J. Immunol. 160: 351–360; Tao et al., 1997, J. Immunol. 158:4237–44; Dozmorov and Miller, 1997, Cell Immunol. 178:187–96; De Bruijn et al., 1992, Eur J Immunol. 22:3013–3020; Houbiers et al., 1993, Eur J Immunol. 26:2072–2077) and macrophage phagocytosed-peptide loaded beads (De Bruijn et al., 1995, Eur J Immunol. 25:1274–1285).

An alternative method for generating in vitro primed immune cells comprises the following steps in the order stated: subjecting live antigenic cells to osmotic shock in vitro; subjecting the antigenic cells to irradiation in vitro; culturing the antigenic cells with immune cells comprising T cells and antigen presenting cells in vitro, wherein the antigenic cells and T cells have at least one common MHC allele, such that primed immune cells are generated.

One source of immune T cells that can be used in the methods of the invention may be obtained in the following manner. Antigenic cells are subjected to an osmotic shock, which consists of incubating the antigenic cells first in a hyperosmotic (hypertonic) buffer, and then in a hypotonic buffer. A hyperosmotic or hypertonic buffer has a higher osmotic pressure relative to the physiological osmotic pressure of a cell. A hypotonic buffer has a lower osmotic pressure than the physiological osmotic pressure in a cell. The physiological osmotic pressure of a cell is that exerted by 0.155 M sodium chloride, which is equivalent to the osmotic pressure of a solution having 0.31 M sucrose (unlike sucrose, sodium chloride dissociates into two ions; the number of solute particles per unit volume determines the osmotic pressure).

The equation relating osmotic pressure of a solution to solute concentration may be written as $\pi = MRT$, wherein $\pi$=osmotic pressure, M=molarity of solute particles in moles of solute particles per liter solvent, R=gas constant and T=temperature in ° K.

Any solutes, buffer systems and procedures that can be used to subject antigenic cells to a change in osmotic pressure can be used in the present methods. The hyperosmotic and hypotonic buffers, and time and temperature of incubations are chosen such that the cells are not ruptured. It is preferred that the temperature of incubation in both the hyperosmotic buffer and the hypotonic buffer is 37° C. It is further preferred that the osmotic pressure of the hyperosmotic buffer in which the antigenic cells are incubated falls within the range of 2 to 5 times, and is most preferably about three times, that of the physiological osmotic pressure.

When the cell is placed in a hyperosmotic buffer, the chemical potential of water in the cell is more than outside, and water flows out of the cell. In hypotonic media, the flow goes in the other direction with water entering the cell. As a result of the change in osmotic pressure, the antigenic cells undergo first shrinkage and then expansion but without rupture of the cells. The osmotically-shocked antigenic cells are then irradiated.

A preferred and exemplary, non-limiting protocol for carrying out the osmotic shock and irradiation is provided hereinbelow:

The cancer or infected cells (e.g., $2 \times 10^6$ cells) are incubated at 37° C. for 5 to 60 minutes in a hyperosmotic buffer (0.5 ml per $2 \times 10^6$ cells) containing 0.5 M sucrose, 10% w/v polyethylene glycol 1000, 10 mM HEPES in tissue culture medium, such as RPMI 1640. (Alternatively, any solutes can be used to prepare a hyperosmotic buffer that would exert a similar osmotic pressure, e.g., about three times physiologic osmotic pressure.) In order to reverse the osmotic effect rapidly, the medium containing the cells is diluted by adding 30 times the volume of a hypotonic buffer (15 ml per $2 \times 10^6$ cells) consisting of 60% tissue culture medium in water. The cells are then incubated at 37° C., e.g., for 1–10 minutes, before they are collected by centrifugation at 500–5000 rpm in a standard laboratory centrifuge. The antigenic cells are not ruptured at the end of this process. The osmotically-shocked antigenic cells are resuspended in culture medium (5 ml for $2 \times 10^6$ cells) and allowed to recover for 0.5 to 24 hours at 37° C., 5% $CO_2$.

After the osmotic shock, the antigenic cells (e.g., one to two million) are irradiated with 1,000 to 10,000 rads in culture medium containing 5% fetal calf serum, and then washed in culture medium containing 10% fetal calf serum. For example, the antigenic cells are irradiated for 30 minutes using a Gammator 50 set to deliver 800 rads/min. Antigenic cells that are subjected to osmotic shock, followed by irradiation are referred to herein as mock-loaded antigenic cells.

The in vitro priming reaction is carried out by culturing the mock-loaded cells with an immune cell composition comprising T cells and antigen presenting cells of a subject. As described in section 5.2, immune cells can be obtained from the spleen or preferably, peripheral blood. If lymphoid tissues or organs are used as a source of immune cells, it is preferable to disperse the cells so as to form a single cell suspension prior to use.

A preferred and exemplary, non-limiting protocol for carrying out the in vitro priming reaction is provided hereinbelow:

Approximately $1 \times 10^6$ cancer or infected cells treated as described above (with osmotic shock and irradiation) are used to prime $1 \times 10^8$ immune cells (e.g., whole blood from which the red blood cells and serum have been removed). The cells are mixed and co-cultured at 37° C., 5% $CO_2$, for preferably 3–9 days, preferably in multiwell plates. The ratio of treated cells to immune cells in the mixed cell culture is preferably 1:100, and may be adjusted to optimize the ratio for generation of responding T cells. Optionally, noncovalent complexes of heat shock protein and peptides isolated from cells that are the same as the antigenic cells, or noncovalent complexes of heat shock protein and exogenous antigenic peptides, are added to the mixed cell culture to enhance the efficiency of the in vitro priming reaction. HSP-antigen complexes can be isolated or prepared in vitro by methods described herein. A concentration range of 1–50 μg heat shock protein peptide complex per ml culture medium is preferred. After several days in culture, e.g., on day six, a $^{51}Cr$ release assay, cytokine secretion, or any other suitable assay known in the art may be performed if desired, to test for antigen-reactive CD4+ T cell activity in the mixed cell culture.

Any methods known in the art may be used to maintain the responding T cell clones. Culture medium for mouse cells usually includes fetal calf serum (FCS) at concentrations ranging from 2 to 10% and 2-mercaptoethanol, usually at $5 \times 10^{-5}$ M. Human cell cultures are usually prepared in medium containing 10 to 20% pooled human serum, although FCS at 10% is an adequate substitute for pooled human serum. Antibiotics, usually penicillin (100 μg/ml) and streptomycin (100 U/ml), may be used. HEPES (25 mM) or morpholinopropane-sulfonic acid (MOPS) (10 mM) can be used to buffer the medium. Suitable culture media and conditions are well known in the art.

To enhance or sustain activity and/or proliferation of the antigen reactive T cells, the mixed cell culture can optionally be restimulated with antigenic cells in the presence of primed immune cells after many days in culture, for example, on day 9 or 10. The antigenic cells used for restimulation need not be osmotically shocked, but should be irradiated. optionally, primed T cells (which are substantially suspended in the culture medium) can be recovered from the mixed cell culture by centrifugation of the culture medium, and restimulated by incubation with freshly irradiated antigenic cells in fresh culture medium at any of various responding T cell/antigenic cell ratios, such as, for example, 100:1. The incubation is preferably also in the presence of lymphokine(s), e.g., purified IL-2 and/or concanavalin A (con A)—stimulated spleen cell supernatant or conditioned medium from activated T cell culture.

Preferably, human IL-2 is used with human cells. By repeated stimulations for example, carried out every 3 to 9 days, a continuous antigen-reactive T cell culture or T cell line with specificity for the antigens present on the antigenic cells can be maintained or established. Standard methods of T cell cloning and clonal expansion may be applied to further propagate these antigen-reactive T cells. See generally, Fathman et al., 1989, in Chapter 30, in "Fundamental Immunology" 2nd edition, ed. Paul, W. E., Raven Press, New York, pp 803–815. The cells can be tested for reactivity on day six after restimulation.

Primed immune cells can be any MHC haplotype-matched immune cells, preferably comprising antigenic presenting cells, or less preferably allogeneic immune cells sharing at least one MHC allele with the immune cells, and are typically obtained from peripheral blood leukocytes or the spleen by standard techniques. The feeder cells are preferably irradiated prior to use.

T cell cultures or cloned T cells primed by the methods of the invention can be stored frozen in liquid nitrogen for at least several years. For example, T cells, preferably during the early log phase of growth, are centrifuged and resuspended in medium containing 10% dimethyl sulfoxide (DMSO) at 4C. Survival of frozen cells is probably greater if the serum concentration of the medium is at least 10%. For example, briefly, 24 hr after antigen exposure, T cells are harvested and resuspended in pre-cooled RPMI supplemented with 20% FCS and 10% dimethyl sulfoxide. By way of example, cells are frozen at a rate of approximately 10° C. per minute by placing them in a styrofoam box in a −70° C. Revco freezer. Such frozen cells should preferably be stored in liquid nitrogen.

For maintenance, T cell clones of interest can be expanded in multiwell plates and subsequently in tissue culture flasks. Briefly, by way of example and not limitation, for expansion, cells are harvested at intervals of 10 to 14 days, readjusted to $1 \times 10^5$ T cells/ml, and restimulated in the presence of feeder cells with newly irradiated antigenic cells and 10 units IL-2/ml. Cells are fed with fresh medium containing IL-2 every 5 days. Unlike macrophages which are adherent to the plates, T cells are non-adherent and can be substantially separated from macrophages by. collecting the cell culture medium. Occasionally, cells grow rapidly and require repeated splitting when cell density exceeds $5 \times 10^5$ per ml.

T cells made by the above methods may be used as a source of T cells for the methods of the invention that can be further co-cultured with pulsed-APCs.

5.3 GENERATION OF ANTIGEN-REACTIVE T CELLS

Antigen-reactive T cells are generated in vitro by stimulation and proliferation of a subset of T cells according to the methods described herein. After sufficient time is given for the in vitro stimulation reaction to occur, the T cells can be tested for proliferation, cytotoxicity, cytokine secretion. Alternately, cells may be restimulated to enhance or sustain the proliferation, or stored or maintained in long-term culture for later use.

Any antigenic cell, e.g., cancer or infected cells described in section 5.1, may be used in the present methods. As described in section 5.1, supra, the source of the antigenic cells may be selected, depending on the nature of the disease with which the antigen is associated, and the intended use of the resulting antigen-reactive T cells. In one embodiment of the invention, any tissues, or cells isolated from a cancer, including cancer that has metastasized to multiple sites, can be used in the present method. In another embodiment of the invention, any cell that is infected with a pathogen, in particular, an intracellular pathogen, such as a virus, bacterium, fungus, parasite, or protozoan, can be used. Typically, by way of example but not limitation, cancer cells can be isolated from a tumor that is surgically removed from a human patient who will be the recipient of the antigen-reactive T cells. Prior to use, solid cancer tissue, pathogen-infected tissue or aggregated cancer cells should be dispersed, preferably mechanically, into a single cell suspension by standard techniques. Enzymes, such as but not limited to, collagenase and Dnase may also be used to disperse cancer cells. Typically, approximately two to three million antigenic cells are used per priming reaction in the method. Thus, if necessary, the cancer or infected cells may be cultured by standard techniques under growth conditions in vitro to obtain the desired number of cells prior to use. Primary tissue or cell lines can also be used.

In a preferred embodiment, the present invention provides a method for generating antigen-reactive T cells comprising the following steps in the order stated: priming immune cells in vivo or in vitro; enriching for subpopulations of immune cells such as CD4+ and APCs;

subjecting APCs to pulsing in vitro with an HSP-antigen complex; co-culturing the pulsed APCs with CD4+ T cells wherein the antigen presenting cells and CD4+ T cells have at least one common MHC allele, such that antigen-reactive CD4+ T cells are generated.

The in vivo priming reaction of the present invention can be carried out by several methods, as described in section 5.2.1. These methods include, immunization of an animal or human recipient with a heat shock protein (HSP) preparation in which the preparation comprises one or more antigenic peptides of interest. In an alternate method for in vivo priming reaction, immunization of the recipient is performed using lysates or extracts derived from antigenic cells.

The primed immune cells are collected from the immunized animal and may be subjected to enrichment for specific populations of cells. Purification or enrichment of subsets of immune cells can be performed by methods known in the art. In a specific example, separation of immune cells is performed by FACS (fluorescence activated cell sorter) analysis using anti-CD4 monoclonal antibody or anti-CD8 monoclonal antibody to select for immune cells comprising CD4+ or CD8+ T cells respectively. In an another embodiment, immune cells are separated by density gradient centrifugation, or affinity chromatography using an immobilized antibody to the CD8 or CD4 marker present on the T cell surface. In an alternate example, CD4+ T cells are selected by co-culturing immune cells with antigen presenting cells such as irradiated syngeneic spleen cells as feeder cells in the presence of antigen such as cancer cell lysate (see section 6).

Additionally, APCs can be enriched by similar methods using cell surface makers specific to the APCs of interest. For example, macrophages may be enriched by the methods described infra or by standard methods in the art, by use of the Mac1 cell surface marker.

Following enrichment of cell populations, the APC rich populations are pulsed with the HSP-antigen complexes prepared from antigenic cells. In a preferred embodiment, the HSP-antigen complexes are substantially purified. In another preferred embodiment, the HSP-antigen complex is prepared in vitro by reconstituting HSP and exogenous antigen as described in Section 5.4.4.

In order to pulse the APC population with antigen, the source of antigen of the invention includes but is not limited to a) substantially purified complex of a heat shock protein and an antigenic molecule; b) HSP-antigen complex present from a cell lysate or extract; c) purified HSP-antigen complex; and d) an exogenously prepared complex of an HSP and antigenic molecule. The pulsing reaction may be accomplished in several ways. APC exposure to HSP-antigen complex may include addition of HSP-antigen complex to in vitro cultured primed immune cell, mixture of HSP-antigen complex derived from antigenic cell lysate with APCs or primed immune cells in vitro, or adding purified HSP-antigen complexes to in vitro cultured APCs or primed immune cells. In a most preferred embodiment, the pulsing of an APC is performed with the identical form of HSP-antigen complex to that used in the in vivo priming reaction. In an alternate embodiment, the pulsing reaction is carried out with a source of HSP-antigen complex comprising an antigenic peptide identical to one or more antigenic peptides of the in vivo priming reaction.

The stimulation and restimulation of selected populations of T cells are provided by the methods of the invention. Stimulation and restimulation of either antigen-reactive CD4+ or antigen-reactive CD8+ T cells in vitro is accomplished by co-culturing of T cells with antigen presenting cells pulsed with HSP-antigen complexes. Co-culturing of T cells with APCs in vitro leads to the expansion of stimulated T cells resulting in antigen-reactive T cells of the invention.

In order to optimize antigen-reactive T cell expansion, the ratio of APC cells in the mixed cell culture is preferably 1:10, and may be adjusted to optimize the ratio for generation of antigen-reactive T cells, after measuring the resulting reactivity of the responding T cells at various ratios. Optionally, non-covalent complexes of heat shock protein and peptides isolated from cells that are the same as the antigenic cells, or non-covalent complexes of heat shock protein and exogenous antigenic peptides, are added to the mixed cell culture to enhance the efficiency of the in vitro stimulation reaction. Heat shock protein-peptide complexes can be isolated or prepared in vitro by methods described in the next section. A concentration range of 1–50 $\mu$g heat shock protein peptide complex per ml culture medium is preferred. The co-culturing is performed under standard conditions of temperature, humidity, $CO_2$ concentration shown in the art. After several days in culture, e.g., on day six, a $^{51}Cr$ release assay or any other suitable assay known in the art may be performed if desired, to test for T cell activity in the mixed cell culture. Alternately, T cells may be assayed for cytotoxicity, cytokine secretion, or proliferation by methods standard in the art (also see section 6, infra).

Any methods known in the art may be used to maintain the responding antigen-reactive T cell clones. Culture medium for mouse cells usually includes fetal calf serum (FCS) at concentrations ranging from 2 to 10% and 2-mercaptoethanol, usually at $5 \times 10^{-5}$ M. Human cell cultures are usually prepared in medium containing 10 to 20% pooled human serum, although FCS at 10% is an adequate substitute for pooled human serum. Antibiotics, usually penicillin (100 $\mu$g/ml) and streptomycin (100 U/ml), may be used. HEPES (25 mM) or morpholinopropane-sulfonic acid (MOPS) (10 mM) can be used to buffer the medium. Suitable culture media and conditions are well known in the art.

To enhance or sustain activity or proliferation of the stimulated antigen-reactive T cells, the mixed cell culture can optionally be restimulated with primed immune cells comprising antigen presenting cells after many days in culture, for example, on day 9 or 10. Any of the sources of HSP-antigen complex described infra, may be used for restimulation. Optionally, antigen-reactive T cells (which are substantially suspended in the culture medium) can be recovered from the mixed cell culture by centrifugation of the culture medium, and restimulated by incubation with freshly irradiated APCs in the presence of HSP-antigen complex, in fresh culture medium at any of various responding T cell/antigenic cell ratios, such as, for example, 10:1. The incubation is preferably also in the presence of lymphokine(s), e.g., purified IL-2 and/or concanavalin A (con A)—stimulated spleen cell supernatant or conditioned medium from stimulated T cell culture. Preferably, human IL-2 is used with human cells. By repeated stimulations for example, carried out every 3 to 9 days, a continuous antigen-reactive T cell culture or T cell line with specificity for the antigens present on the antigenic cells/APCs can be maintained or established. Standard methods of T cell cloning and clonal expansion may be applied to further propagate these antigen-reactive T cells. See generally, Fathman et al., 1989, in Chapter 30, in "Fundamental Immunology" 2nd edition, ed. Paul, W. E., Raven Press, New York, pp 803–815. The cells can be tested for reactivity on day six after restimulation.

Primed immune cells for the purpose of restimulation can be any MHC haplotype-matched immune cells, comprising antigenic presenting cells, or less preferably allogeneic immune cells sharing at least one MHC allele with the immune cells, and are typically obtained from peripheral blood leukocytes or the spleen by standard techniques. The feeder cells are preferably irradiated prior to use.

Spleen cells stimulated with concanavalin A (Con A) yield culture supernatant containing rather high levels of IL-2. By way of example, to prepare rat Con A SF, rat spleen cells are cultured at a density of $1.25 \times 10^6$ cells/ml in medium (DMEM, RPMI, or other suitable medium) containing 2 to 10% fetal calf serum (FCS) and $5 \times 10^{-5}$ M 2-mercaptoethanol. Con A (Pharmacia Fine Chemicals, Inc., Uppsala, Sweden) is added to give a final concentration of 2.5 to 5 $\mu$g/ml. After 48 hr, the culture supernatant is collected and centrifuged. Lymphokines other than IL-2, including colony stimulating factor and growth factors for B cells, may also be present as well in Con A SF. Such supernatant are useful for the initial cloning of T cells and for maintaining cloned T cells.

Recombinant human or murine IL-2 can be purchased commercially. Also, by way of example, human IL-2 can be prepared by culturing peripheral blood leukocytes or spleen cells ($5 \times 10^6$ per ml) in RPMI 1640 supplemented as above with PHA-P (Difco Laboratories, Detroit, Mich.) at a final concentration of 0.2%. IL-2-containing supernatant is collected by centrifugation after culture for 48 hr.

T cell cultures or cloned antigen-reactive T cells prepared by the methods of the invention can be stored frozen in liquid nitrogen for at least several years. For example, T cells, preferably during the early log phase of growth, are centrifuged and resuspended in medium containing 10% dimethyl sulfoxide (DMSO) at 4° C. Survival of frozen cells is probably greater if the serum concentration of the medium is at least 10%. For example, briefly, 24 hr after antigen exposure, T cells are harvested and resuspended in pre-cooled RPMI supplemented with 20% FCS and 10% dimethyl sulfoxide. By way of example, cells are frozen at a rate of approximately 1° C. per minute by placing them in a styrofoam box in a −70° C. Revco freezer. Such frozen cells should preferably be stored in liquid nitrogen.

For maintenance, T cell clones of interest can be expanded in multiwell plates and subsequently in tissue culture flasks. Briefly, by way of example and not limitation, for expansion, cells are harvested at intervals of 10 to 14 days, readjusted to $1 \times 10^5$ T cells/ml, and restimulated in the presence of primed immune cells with newly irradiated antigenic cells and 10 units IL-2/ml. Cells are fed with fresh medium containing IL-2 every 5 days. Unlike macrophages which are adherent to the plates, T cells are non-adherent and can be substantially separated from macrophages by collecting the cell culture medium. Occasionally, cells grow rapidly and require repeated splitting when cell density exceeds $5 \times 10^5$ per ml.

5.4 PREPARATIONS OF HEAT SHOCK PROTEIN-ANTIGEN COMPLEXES

In an embodiment wherein heat shock protein (HSP)-peptide complexes isolated from antigenic cells are desired to be used for priming and/or pulsing, or to be added to the mixed cell culture, the HSPs that can be used include but are not limited to, HSP60, HSP70, HSP90, HSP100, and gp96, alone or in combination. Preferably, the HSPs are human HSPs.

Heat shock proteins (HSPs), which are also referred to interchangeably as stress proteins, useful in the practice of the instant invention can be selected from among any cellular protein that satisfies any one of the following criteria. It is a protein whose intracellular concentration increases when a cell is exposed to a stressful stimuli, it is capable of binding other proteins or peptides, and it is capable of releasing the bound proteins or peptides in the presence of adenosine triphosphate (ATP) or low pH; or it is a protein showing at least 35% homology with any cellular protein having any of the above properties.

Any methods known in the art can be employed to substantially purify endogenous HSP-peptide complexes from antigenic cells, e.g., cancer cells or infected cells, for use in the present methods. For example, the purification of HSP70-peptide complexes has been described previously, see, for example, Udono et al., 1993, J. Exp. Med. 178:1391–1396. See also International Publication No. WO 95/24923 dated Sep. 21, 1995.

Another method that can be applied for the substantial purification of heat shock protein-peptide complexes, such as HSP70-peptide complexes, comprises contacting cellular proteins with ADP or a nonhydrolyzable analog of ATP affixed to a solid substrate, such that HSP70 in the lysate can bind to the ADP or nonhydrolyzable ATP analog, and eluting the bound HSP70. A preferred method uses column chromatography with ADP affixed to a solid substratum (e.g., ADP-agarose). Thus, HSP70-peptide complexes can be readily obtained from cancer cells or cells infected by an infectious agent or other cells by a rapid, one-step ADP-agarose chromatography. For example, Meth A sarcoma cells (500 million cells) can be homogenized in hypotonic buffer and the lysate is centrifuged at 100,000 g for 90 minutes at 4° C. The supernatant is applied to an ADP-agarose column. The columns are washed in buffer and are eluted with 3 mM.

These protocols may be used to isolate HSPs from any eukaryotic cells, for example, tissues, isolated cells or immortalized eukaryotic cell lines infected with a pathogen, tumor cells or tumor cell lines, and eukaryotic cells transfected with a gene encoding and expressing a tumor-specific antigen, tumor-associated antigen or an antigen of the pathogen.

Furthermore, antigenic molecules, either purified from natural sources or chemically synthesized or recombinantly produced, may be reconstituted with a variety of naturally purified or chemically synthesized or recombinantly produced heat shock proteins in vitro to generate immunogenic non-covalent heat shock protein-peptide molecule complexes. Methods for non-covalently complexing a HSP and an exogenous antigenic molecule in vitro is described in Section 5.4.4.

Heat shock protein-peptide complexes isolated from antigenic cells or produced in vitro can be used during the initial in vivo priming reaction, and/or during any of the subsequent pulsing or stimulation/restimulation steps.

5.4.1 PREPARATION AND PURIFICATION OF HSP 70-PEPTIDE COMPLEXES

The purification of HSP 70-peptide complexes has been described previously, see, for example, Udono et al., 1993, *J. Exp. Med.* 178:1391–1396. A procedure that may be used, presented by way of example but not limitation, is as follows:

Initially, tumor cells are suspended in 3 volumes of 1× Lysis buffer consisting of 5 mM sodium phosphate buffer (pH7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with phosphate buffered saline (PBS) containing 2 mM $Ca^{2+}$ and 2 mM $Mg^{2+}$. When the cells are lysed by mechanical shearing the supernatant is diluted with an equal volume of 2× Lysis buffer prior to mixing with Con A Sepharose. The supernatant is then allowed to bind to the Con A Sepharose for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC column equilibrated in 20 mM Tris-Acetate pH 7.5, 20 mM NaCl, 0.1 mM EDTA and 15 mM 2-mercaptoethanol. The column is then developed with a 20 mM to 500 mM NaCl gradient and then eluted fractions fractionated by sodium dodecyl sulfate-polyacrylamide gel electrophoresis (SDS-PAGE) and characterized by immunoblotting using an appropriate anti-HSP70 antibody (such as from clone N27F3–4, from StressGen).

Fractions strongly immunoreactive with the anti-HSP70 antibody are pooled and the HSP70-peptide complexes precipitated with ammonium sulfate; specifically with a 50%–70% ammonium sulfate cut. The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a Sephadex$^R$ G25 column (Pharmacia). If necessary the HSP70 preparation thus obtained can be repurified through the Mono Q FPCL Column as described above.

The HSP70-peptide complex can be purified to apparent homogeneity using this method. Typically 1 mg of HSP70-peptide complex can be purified from 1 g of cells/tissue.

The present invention further describes a new and rapid method for purification of HSP70-peptide complexes. This improved method uses chromatography with ADP affixed to a solid substratum (e.g., ADP-agarose). The resulting HSP70 preparations are higher in purity and devoid of peptides. The HSP70 yields are also increased significantly by about more than 10 fold. Alternatively, chromatography with nonhydrolyzable analogs of ATP, instead of ADP, can be used in chromatography for purification of HSP70-peptide complexes. By way of example but not limitation, purification of HSP70-peptide complexes by ADP-agarose chromatography was carried out as follows: Meth A sarcoma cells (500 million cells) were homogenized in hypotonic buffer and the lysate was centrifuged at 100,000 g for 90 minutes at 4° C. The supernatant was divided into two and was applied to an ADP-agarose or an ATP-agarose column. The columns were washed in buffer and were eluted with 3 Mm ADP or 3 mM ATP, respectively. The eluted fractions were analyzed by SDS-PAGE: in both cases, apparently homogeneous preparations of HSP70 were obtained. However, when each of the preparations was tested for presence of peptides, the ADP-bound/eluted HSP70 preparation was found to be associated with peptides, while the ATP-bound/eluted HSP70 preparation was not.

5.4.2 PREPARATION AND PURIFICATION OF HSP 90-PEPTIDE COMPLEXES

A procedure that can be used, presented by way of example and not limitation, is as follows:

Initially, tumor cells are suspended in 3 volumes of 1× Lysis buffer consisting of 5 mM sodium phosphate buffer pH 7, 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with PBS containing 2 mM $Ca^{2+}$ and 2 mM $Mg^{2+}$. When the cells are lysed by mechanical shearing the supernatant is diluted with an equal volume of 2× Lysis buffer prior to mixing with Con A Sepharose. The supernatant is then allowed to bind to the Con A Sepharose for 2–3 hours at 4° C. The material that fails to bind is harvested and dialyzed for 36 hours (three times, 100 volumes each time) against 20 mM sodium phosphate pH 7.4, 1 mM EDTA, 250 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC column equilibrated with lysis buffer. The proteins are then eluted with a salt gradient of 200 mM to 600 mM NaCl.

The eluted fractions are fractionated by SDS-PAGE and fractions containing the HSP90-peptide complexes identified by immunoblotting using an anti-HSP90 antibody such as 3G3 (Affinity Bioreagents). HSP90-peptide complexes can be purified to apparent homogeneity using this procedure. Typically, 150–200 μg of HSP90-peptide complex can be purified from 1 g of cells/tissue.

5.4.3 PREPARATION AND PURIFICATION OF GP96-PEPTIDE COMPLEXES

A procedure that can be used, presented by way of example and not limitation, is as follows:

A pellet of tumors is resuspended in 3 volumes of buffer consisting of 30 mM sodium bicarbonate buffer (pH 7.5) and 1 mM PMSF and the cells allowed to swell on ice 20 minutes. The cell pellet then is homogenized in a Dounce homogenizer (the appropriate clearance of the homogenizer will vary according to each cells type) on ice until >95% cells are lysed.

The lysate is centrifuged at 1,000 g for 10 minutes to remove unbroken cells, nuclei and other debris. The supernatant from this centrifugation step then is recentrifuged at 100,000 g for 90 minutes. The gp96-peptide complex can be purified either from the 100,000 pellet or from the supernatant.

When purified from the supernatant, the supernatant is diluted with equal volume of 2× lysis buffer and the supernatant mixed for 2–3 hours at 4° C. with Con a sepharose equilibrated with PBS containing 2 mM $Ca^{2+}$ and 2 mM $Mg^{2+}$. Then, the slurry is packed into a column and washed with 1× lysis buffer until the $OD_{280}$ drops to baseline. Then, the column is washed with ⅓ column bed volume of 10% α-methyl mannoside (α-MM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDS-PAGE. Typically the resulting material is about 60–95% pure; however, this depends upon the cell type and the tissue-to-lysis buffer ratio used. Then the sample is applied to a Mono Q FPLC column (Pharmacia) equilibrated with a buffer containing 5 mM sodium phosphate, pH 7. The proteins then are eluted from the column with a 0–1M NaCl gradient and the gp96 fraction elutes between 400 mM and 550 mM NaCl.

The procedure, however, may be modified by two additional steps, used either alone or in combination, to consistently produce apparently homogeneous gp96-peptide complexes. One optional step involves an ammonium sulfate precipitation prior to the Con A purification step and the other optional step involves DEAE-Sepharose purification. after the Con A purification step but before the Mono Q FPLC step.

In the first optional step, the supernatant resulting from the 100,000 g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A Sepharose and the procedure followed as before.

In the second optional step, the gp96 containing fractions eluted from the Con A column are pooled and the buffer exchanged for 5 mM sodium phosphate buffer, pH 7, 300 mM NaCl by dialysis, or preferably by buffer exchange on a Sephadex G25 column. After buffer exchange, the solution is mixed with DEAE-Sepharose previously equilibrated with 5 mM sodium phosphate buffer, pH 7, 300 mM NaCl. The protein solution and the beads are mixed gently for 1 hour and poured into a column. Then, the column is washed with 5 mM sodium phosphate buffer, pH 7, 300 mM NaCl, until the absorbance at 280 mM drops to baseline. Then, the bound protein is eluted from the column with five volumes of 5 mM sodium phosphate buffer, pH 7, 700 mM NaCl. Protein containing fractions are pooled and diluted with 5 mM sodium phosphate buffer, pH 7 in order to lower the salt concentration to 175 mM. The resulting material then is applied to the Mono Q FPLC column (Pharmacia) equilibrated with 5 mM sodium phosphate buffer, pH 7 and the protein that binds to the Mono Q FPLC column (Pharmacia) is eluted as described before.

It is appreciated, however, that one skilled in the art may assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000 g pellet, the pellet is suspended in 5 volumes of PBS containing either 1% sodium deoxycholate or 1% oxtyl glucopyranoside (but without the $Mg^{2+}$ and $Ca^{2+}$) and incubated on ice for 1 hour. The suspension is centrifuged at 20,000 g for 30 minutes and the resulting supernatant dialyzed against several changes of PBS (also without the $Mg^{2+}$ and $Ca^{2+}$) to remove the detergent. The dialysate is centrifuged at 100,000 g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000 g supernatant, see above.

The gp96-peptide complexes can be purified to apparent homogeneity using this procedure. About 10–20 μg of gp96 can be isolated from 1 g cells/tissue.

5.4.4 IN VITRO PRODUCTION OF HSP-ANTIGENIC MOLECULE COMPLEXES

An additional source of HSP-antigen complex include complexes of HSPs and antigenic molecules produced in vitro. As will be appreciated by those skilled in the art, the antigenic molecules either isolated by the procedures known in the art, or chemically synthesized, or recombinantly produced, may be reconstituted with a variety of naturally purified or recombinant HSPs in vitro to generate immunogenic non-covalent HSP-antigenic molecule complexes. Alternatively, exogenous antigens or antigenic/immunogenic fragments or derivatives thereof can be non-covalently complexed to HSPs for use in the generation of antigen-reactive T cells of the invention. A preferred, exemplary protocol for noncovalently complexing a HSP and an antigenic molecule in vitro is discussed below.

Prior to complexing, the HSPs are pretreated with ATP or low pH to remove any peptides that may be associated with the HSP of interest. When the ATP procedure is used, excess ATP is removed from the preparation by the addition of apyranase as described by Levy, et al., 1991, *Cell* 67:265–274. When the low pH procedure is used, the buffer is readjusted to neutral pH by the addition of pH modifying reagents.

The antigenic molecules (1 μg) and the pretreated HSP (9 μg) are admixed to give an approximately 5 antigenic molecule: 1 HSP molar ratio. Then, the mixture is incubated for 15 minutes to 3 hours at 4°–45° C. in a suitable binding buffer, for example, one containing 20 mM sodium phosphate, pH 7.2, 350 mM NaCl, 3 mM MgcL2 and 1 mM phenyl methyl sulfonyl fluoride (PMSF). The preparations are centrifuged through Centricon 10 assembly (Millipore) to remove any unbound peptide. The association of the peptides with the HSPs can be assayed by SDS-PAGE. This is the preferred method for in vitro complexing of peptides isolated from MHC-peptide complexes of peptides disassociated from endogenous HSP-peptide complexes.

In an alternative embodiment of the invention, preferred for producing complexes of HSP70 to exogenous antigenic molecules such as proteins, 5–10 micrograms of purified HSP is incubated with equimolar quantities of the antigenic molecule in 20 mM sodium phosphate buffer pH 7.5, 0.5M NaCl, 3 mM $MgCl_2$ and 1 mM ADP in a volume of 100 microliter at 37° C. for 1 hr. This incubation mixture is further diluted to 1 ml in phosphate-buffered saline.

In an alternative embodiment of the invention, preferred for producing complexes of gp96 or HSP90 to peptides, 5–10 micrograms of purified gp96 or HSP90 is incubated with equimolar or excess quantities of the antigenic peptide in a suitable buffer such as one containing 20 mM sodium phosphate buffer, pH 7.5, 0.5M NaCl, 3 mM $MgCl_2$ at 60°–65° C. for 5–20 minutes. This incubation mixture is allowed to cool to room temperature and centrifuged more than once, if necessary through Centricon 10 assembly (Millipore) to remove any unbound peptide.

Following complexing, the HSP-antigenic molecule complexes can be used in the various methods of the instant invention.

5.5 DETERMINATION OF REACTIVITY OF RESPONDING T CELLS

In an optional procedure, after the in vitro stimulation/restimulation reaction, the mixed cell culture comprising responding T cells including the antigen-reactive T cells of the invention can be assayed for reactivity using a $^{51}Cr$ release assay, a cytokine assay, or any assay known in the art for measuring reactivity of immune effector cells.

By way of example but not limitation, the following four (4) hour $^{51}Cr$-release assay can be used (see, Palladino et al., 1987, Cancer Res. 47:5074–5079 and Blachere et al., 1993, J. Immunotherapy 14:352–356). In this assay, cells in the stimulated co-culture, i.e., the effector T cells, are added to a target cell suspension to give various effector:target (E:T) ratios (usually from 1:1 to 40:1). The target cells are prelabelled by incubating $1 \times 10^6$ target cells in culture medium containing 200 mCi $^{51}Cr$/ml for one hour at 37° C. The labelled cells are washed three times following labeling. Each assay point (E:T ratio) is performed in triplicate. The controls measure spontaneous $^{51}Cr$ release wherein no lymphocytes are added to the assays, and 100% release wherein the labelled target cells are lysed with detergent, such as TNEN (10 mM Tris-Hcl, 250 mM NaCl, 0.1 mM EDTA and 1% NP-40). After incubating the effector/target cell mixtures for 4 hours, the cells are collected by centrifugation at 200 g for 5 minutes. The amount of $^{51}Cr$ released into the supernatant is measured by a gamma counter. The percent cytotoxicity is measured as cpm in the test sample minus spontaneously released cpm divided by the total detergent released cpm minus spontaneously released cpm.

$$\% \text{ cytotoxicity} = \frac{\text{cpm of test sample minus cpm of spontaneous }^{51}Cr \text{ release}}{\text{cpm of maximal }^{51}Cr \text{ release minus cpm of spontaneous }^{51}Cr \text{ release}} \times 100$$

Alternatively, the reactivity of the responding T cells can also be determined by measuring the levels of cytokines, such as but not limited to tumor necrosis factor, granulocyte-macrophage colony stimulating factor, interleukin-2, and interleukin-5 secreted upon stimulation or restimulation. Proliferation of T cells may also be examined by standard methods in the art, such as 3H-thymidine incorporation, FACS analysis, growth curves, and cytokine secretion.

5.6 REINFUSION OF ANTIGEN-REACTIVE T CELLS

The antigen-reactive T cells of the invention, are infused into a recipient systemically, preferably intravenously, by conventional clinical procedures. In a specific embodiment, the T cell population that was suspended in the culture medium is administered to the patient. Alternatively and optionally, antigen-reactive T cells can be purified prior to administration by any standard methods, such as but not limited to, density gradient centrifugation, and affinity chromatography using an immobilized antibody to the CD4 or CD8 antigen present on the antigen-reactive T cells. The antigen-reactive T cells are infused, preferentially by systemic administration into the recipient. Recipients generally receive from about $10^5$ to about $10^{11}$ purified antigen-reactive T cells (or a composition comprising the same) per administration, and preferably about $10^6$ to about $10^8$ immune cells per administration or about $10^5$ to about $10^7$ purified antigen-reactive T cells (or a composition comprising the same) per administration, depending on the condition of the patient. Preferably, such T cells are administered to an autologous recipient.

The subject or recipient is preferably an animal, including but not limited to animals such as cats, dogs, cows, pigs, mice, rats, monkeys, chickens, etc., and is preferably a mammal, and most preferably human.

Various delivery systems are known and can be used to administer the antigen-reactive T cells of the invention, e.g., encapsulation in liposomes, microparticles, microcapsules. Methods of introduction include but are not limited to intradermal, intramuscular, intraperitoneal, intravenous, subcutaneous, intranasal, and oral routes. The cells may be administered by any convenient route, for example by infusion, and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers. In one embodiment, administration can be by direct injection at the site (or former site) of a cancer or infection, or directly into the cancer or tumor.

The present invention also provides pharmaceutical compositions. Such compositions comprise a therapeutically or prophylactically effective amount of antigen-reactive T cells of the invention, and a pharmaceutically acceptable carrier or excipient. Such a carrier includes but is not limited to saline, culture medium with or without serum, buffered saline, dextrose, water, glycerol, ethanol, and combinations thereof. The carrier and composition can be sterile. The formulation should suit the mode of administration. The composition, if desired, can also contain minor amounts of wetting or emulsifying agents, or pH buffering agents. In a preferred embodiment, the pharmaceutical composition comprises a majority of CD4+ antigen-reactive T cells.

In a preferred embodiment, the composition is formulated in accordance with routine procedures as a pharmaceutical composition adapted for intravenous administration to human beings. Typically, carriers for intravenous administration are sterile isotonic aqueous buffers. Where necessary, the composition may also include a local anesthetic such as lignocaine to ease pain at the site of the injection. Where the composition is to be administered by infusion, it can be dispensed with an infusion bottle containing sterile pharmaceutical grade water, saline or culture medium. Where the composition is administered by injection, an ampoule of sterile water or saline or culture medium for injection can be provided so that the ingredients may be mixed prior to administration.

The amount of antigen-reactive T cells of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration.

In some regimens, patients may optionally receive in addition a suitable dosage of a biological response modifier including but not limited to the interferon-$\gamma$, interferon-$\alpha$, interleukin-2, interleukin-4, interleukin-7, interleukin-10, interleukin-12, tumor necrosis factor, granulocyte-macrophage colony stimulating factor, or other cytokines and growth factors.

5.7 TARGET INFECTIOUS DISEASES

Infectious diseases that can be treated or prevented by antigen-reactive T cells of the present invention are caused by infectious agents including, but not limited to viruses, bacteria, fungi, protozoans and parasites.

Viral diseases that can be treated or prevented by the methods and compositions of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type II (HIV-II)

Bacterial diseases that can be treated or prevented by the methods and compositions of the present invention are caused by bacteria including, but not limited to, mycobacteria rickettsia, mycoplasma, neisseria and legionella.

Protozoal diseases that can be treated or prevented by the methods and compositions of the present invention are caused by protozoa including, but not limited to, leishmania, kokzidioa, and trypanosoma.

Parasitic diseases that can be treated or prevented by the methods and compositions of the present invention are caused by parasites including, but not limited to, chlamydia and rickettsia.

5.8 TARGET CANCERS

Cancers that can be treated or prevented by antigen-reactive T cells and methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrm's macroglobulinemia, and heavy chain disease.

In a specific embodiment, the cancer is metastatic. In another specific embodiment, the cancer is a tumor. In yet another embodiment, the recipient has undergone autologous bone marrow transplantation as a part of cancer therapy.

6. EXAMPLES

The following examples demonstrate methods of the present invention for generating antigen-reactive T cells in vitro, using Meth A (a methylcholanthrene-induced fibrosarcoma) cancer cells in murine strains. The examples further characterize the antigen-reactive T cells, and provide working examples of the methods of the instant invention.

6.1 MATERIALS

The source of antigen for the priming reaction in vivo was Meth A cell lysate emulsified with equal volume CFA (complete Freund's adjuvant) from Meth A (a methylcholanthrene-induced fibrosarcoma) cancer cells. Mice used were BALB/c females 8–10 weeks old, or C57BL/6.

6.2 CHARACTERIZATION OF ANTIGEN-REACTIVE T CELLS

Preparation of antigenic molecules for priming/immunization was carried out as follows. $6 \times 10^7$ Meth A cells per ml were suspended in plain RPMI media and lysed by freeze and thaw 5 times, as per methods commonly known in the art. For each immunization, 100 $\mu$l of total Meth A cell lysate was emulsified in equal volume of CFA. Immunizations with the emulsified lysates were administered subcutaneously to BALB/c mice twice a week. One week after the second immunization, spleen cells from immunized mice were collected and cultured in a 24 well plate ($5 \times 10^6$/well) in the presence of Meth A total cell lysate ($2 \times 10^5$ eq/well). The spleen cells comprise APCs and primed T cells. After 7 days in culture, cells were restimulated by adding irradiated syngeneic spleen cells as feeder cells in the presence of Meth A lysate. After 3–4 rounds of restimulation, proliferating cells were analyzed by FACS using anti-CD4 mAb and anti-CD8 mAb. Results are shown in FIG. 1. The majority cells are CD4+ cells.

In order to further characterize the proliferation of the primed immune cells in vitro, a time course of the proliferative response was performed. In this experiment, T cells resulting from the in vitro spleen cell culture were cultured in the presence of irradiated syngeneic spleen cells in the absence or presence of different amounts of antigen (Meth A cell lysate). $4 \times 10^4$ T cells/well were cultured in a 96 well flat bottom plate. Cells were grown at 37° C. and 5% $CO_2$. Twenty four hours prior to harvest, 0.1 $\mu$Ci/well of $^3$H-thymidine was added to the wells. Incorporation of $^3$H-thymidine was measured by scintillation counting by methods well known in the art. Results as shown in FIG. 2, demonstrate that a maximum proliferative response was obtained at day 4.

With the addition of blocking antibody such as anti-CD4 or anti-I-Ad/I-Ed (1 $\mu$l of mAb added to the 96 well culture at day 0), cell proliferation was inhibited. These results, shown in FIG. 3, indicate that the proliferative T cells were I-Ed restricted CD4+ T cells.

In a further characterization of the proliferative cells described supra, the pattern of cytokine secretion by the cells cultured in the 96 well plates, were examined by ELISA methods known in the art. After 72 hours in culture, the supernatant of the cultures were examined for the presence of cytokines known to be secreted by T cells, such as interron-gamma (IFN$\gamma$). As demonstrated in FIG. 4, IFN$\gamma$ was detected in supernatant cultured in the presence of Meth A lysate.

The antigen specificity of the proliferative cells were investigated by using different cell lysates from either Meth A cells, CMS5 cells or P815 cells. Activity assays using $^3$H-thymidine were performed on day 4 cultures. As demonstrated in FIG. 5, only cells incubated in the presence of Meth A cell lysates incorporated $^3$H-thymidine, thus indicating a proliferative response. Neither CMS5 nor P815 lysates as a source of HSP-antigen complex in vitro were able to induce proliferation of the immune cells primed in vivo with Meth A lysate preparations. These results support the methods of the invention in demonstrating the dependence of antigen specificity in the development of antigen-reactive T cells.

6.3 ANTIGEN RECOGNITION BY CD4+ T CELLS

In section 6.2, CD4+ T cells were demonstrated to proliferate in the presence of Meth A cell lysate when used as a source of antigen. This response has been further characterized in the following section, to demonstrate, by way of example, but not limitation, an interaction of CD4+ T cells with a preparation of gp96-antigen complex of Meth A cells. The example further demonstrates the specificity of the MHC restriction.

Antigen-reactive CD4+ T cells were generated by the methods of the invention resulting in a clonal T cell 320 population herein referred to as 12D1. As demonstrated in FIG. 6, antigen-reactive CD4+ T cells secreted IL-5 when cultured in the presence of Meth A cell cytosol or gp96 derived from Meth A cells, but not in the presence of gp96 derived from D122 Lewis Lung carcinoma cells.

The CD4+ T cell cytokine secretion in response to Meth A cell antigen was inhibited by monoclonal antibodies specific to the CD4+ T cells (see FIG. 7 & 8). Anti-CD4 mAb or anti-I-Ed mAb inhibited T cell cytokine secretion response, whereas other antibodies (such as anti-IAd or anti-CD8) did not. These results demonstrate that antigen-reactive T cells secrete cytokines in response to exposure to antigen such as Meth A cell lysate or gp96 preparation from Meth A cells. Further, these results demonstrate that the MHC restriction is important in the pulsing reaction.

The role of the class II MHC pathway was further investigated by examining the ability of chloroquine (500 $\mu$M) to inhibit the cytokine secretion response. Chloroquine is known in the art as an agent that neutralizes acidic compartments of the cell, which would prevent proteolytic processing of peptides within lysosomes. As discussed herein, class II MHC molecules, involved in CD4+ T cell interactions, bind to antigenic peptides in acidic compartments of the cell. Since chloroquine neutralizes these acidic compartments, this agent is believed to disrupt the class II MHC pathway. In order to examine the effects of chloroquine, splenic APCs, after irradiation were treated with 500 $\mu$M chloroquine, then incubated for 30 minutes at 37° C. or 4° C. FIG. 9 demonstrates that the cytokine secretion response of T cells to Meth A cytosol as a source of antigen, was significantly inhibited by chloroquine. Further, the cytokine secretion response of T cells to Meth A-derived gp96 preparation was completely inhibited by chloroquine.

In order to investigate the requirement of endocytosis of antigens in the CD4+ /MHC II pathway, the effects of paraformaldehyde on the T cell cytokine secretion response was investigated. Paraformaldehyde is a cross-linking reagent that prevents endocytosis of antigen derived from outside the cell. In order to examine the effects of paraformaldehyde, splenic APCs were treated with 1% paraformaldehyde after irradiation, then incubated for 30 minutes at 37° C. or 4° C. Results shown in FIG. 9 demonstrate that the cytokine secretion response of T cells to Meth A cytosol as a source of antigen, was inhibited by paraformaldehyde. Similarly, the cytokine secretion response of T cells to Meth A derived gp96 was also inhibited by paraformaldehyde. These results demonstrated that processing of extracellularly derived gp96 antigen complexes for presentation of antigen by MHC class II molecules proceeds via an endocytic pathway and further supports the methods of the invention. Taken together, FIG. 9 demonstrates that both processing and internalization of antigen were required in the class II MHC pathway of the invention.

In order to examine the requirement of MHC matching for the T cell proliferation response, T cells were stimulated with splenic APCs of either BALB/c mice or of C57BL/6 mice. Since BALB/c mice comprise similar MHC haplotypes as the in vitro cultured T cells, the BALB/c splenic APCs stimulated CD4+ T cell proliferation. As demonstrated in FIG. 10, C57BL/6 mice splenic APCs do not support the cytokine secretion response of T cells and demonstrated a requirement for MHC matching. These results support the instant invention by demonstrating that similar MHC classes between T cells and antigen presenting cells supports expansion of T cells in vitro.

In summary, immune cells treated according to the methods of the invention can be stimulated in vitro to produce the antigen-reactive T cells that can mediate an effective antigen-specific T cell response. Thus, administration of such in vitro generated antigen-reactive T cells to a MHC-matched recipient, as described herein, represents a therapeutic or preventative approach for a wide range of cancers or infectious diseases.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for generating T cells reactive to an antigenic molecule, said method comprising:

incubating immune cells comprising T cells and antigen presenting cells in vitro with a purified non-covalent complex of a heat shock protein and said antigenic molecule, wherein the immune cells are obtained from an animal immunized with a molecule displaying the antigenicity of said antigenic molecule, whereby T cells reactive to the antigenic molecule are generated.

2. A method for generating T cells reactive to an antigenic molecule, said method comprising:

incubating immune cells comprising T cells and antigen presenting cells in vitro with a purified non-covalent complex of a heat shock protein and said antigenic molecule, wherein the immune cells are immunized prior to said incubating step in vitro with a molecule displaying the antigenicity of said antigenic molecule, and wherein the antigen presenting cells and T cells have at least one common MCH allele, whereby T cells reactive to the antigenic molecule are generated.

3. A method for generating T cells reactive to an antigenic molecule, said method comprising:

(a) immunizing an animal with said antigenic molecule;
(b) obtaining immune cells from the animal, said immune cells comprising T cells and antigen presenting cells; and
(c) incubating the immune cells in vitro with a purified non-covalent complex of a heat shock protein and a molecule displaying the antigenicity of said antigenic molecule, whereby T cells reactive to the antigenic molecule are generated.

4. A method for generating T cells reactive to an antigenic molecule, said method comprising the following steps in the order presented:

(a) immunizing immune cells comprising antigen presenting cells and T cells in vitro with said antigenic molecule, wherein the antigen presenting cells and T cells have at least one common MHC allele; and
(b) incubating the immune cells in vitro with a purified non-covalent complex of a heat shock protein and a molecule displaying the antigenicity of said antigenic molecule, whereby T cells reactive to the antigenic molecule are generated.

5. A method for generating T cells reactive to an antigenic molecule said method comprising:

(a) immunizing an animal with an antigenic molecule;
(b) obtaining immune cells with the animal, said immune cells comprising T cells;
(c) incubating the immune cells with antigen presenting cells pulsed with a purified non-covalent complex of a heat shock protein and the antigenic molecule, wherein the antigen presenting cells and immune cells have at least one common MHC allele; and
(d) repeating said incubating step at least once by adding said antigen presenting cells pulsed with a purified non-covalent complex of a heat shock protein and the antigenic molecule to said incubated cells resulting from step (c), whereby T cells reactive to the antigenic molecule are generated.

6. A method for generating T cells reactive to an antigenic molecule, said method comprising:

incubating immune cells comprising T cells and antigen presenting cells in vitro with a purified non-covalent complex of a heat shock protein and said antigenic molecule, wherein the immune cells are obtained from an animal immunized with said antigenic molecule, whereby T cells reactive to the antigenic molecule are generated.

7. A method for generating T cells reactive to an antigenic molecule said method comprising:

incubating immune cells comprising T cells and antigen presenting cells in vitro with a purified non-covalent complex of a heat shock protein and said antigenic molecule, wherein the immune cells are immunized prior to said incubating step in vitro with said antigenic molecule, and wherein the antigen presenting cells and T cells have at least one common MHC allele, whereby T cells reactive to the antigenic molecule are generated.

8. A method for generating T cells reactive to an antigenic molecule, said method comprising:

(a) immunizing an animal with said antigenic molecule;
(b) obtaining immune cells from the animal, said immune cells comprising T cells and antigen presenting cells; and
(c) incubating the immune cells in vitro with a purified non-covalent complex of a heat shock protein and said antigenic molecule, whereby T cells reactive to the antigenic molecule are generated.

9. A method for generating T cells reactive to an antigenic molecule, said method comprising the following steps in the order presented:

(a) immunizing immune cells comprising antigen presenting cells and T cells in vitro with said antigenic molecule, wherein the antigen presenting cells and T cells have at least one common MHC allele; and
(b) incubating the immune cells in vitro with a purified non-covalent complex of a heat shock protein and said antigenic molecule, whereby T cells reactive to the antigenic molecule are generated.

10. A method for generating T cells reactive to an antigenic molecule, said method comprising:

incubating immune cells comprising T cells and antigen presenting cells in vitro with a purified non-covalent complex of a heat shock protein and said antigenic molecule, wherein the immune cells are obtained from an animal immunized with one or more antigenic cells expressing said antigenic molecule, whereby T cells reactive to the antigenic molecule are generated.

11. A method for generating T cells reactive to an antigenic molecule, said method comprising:

incubating immune cells comprising T cell and antigen presenting cells in vitro with a purified non-covalent complex of a heat shock protein and said antigenic molecule, wherein the immune dells are immunized prior to said incubating step in vitro with one or more antigenic cells expressing said antigenic molecule, and wherein the antigen presenting cells and T cells have at least one common MHC allele, hereby T cells reactive to the antigenic molecule are generated.

12. A method for generating T cells reactive to an antigenic molecule, said method comprising:

(a) immunizing an animal with one or more antigenic cells expressing said antigenic molecule;
(b) obtaining immune cells from the animal, said immune cells comprising T cells and antigen presenting cells; and (c) incubating the immune cells in vitro with a purified non-covalent complex of a heat shock protein and said antigenic molecule, whereby T cells reactive to the antigenic molecule are generated.

13. A method for generating T cells reactive to an antigenic molecule, said method comprising the following steps in the order presented:
   (a) immunizing immune cells comprising antigen presenting cells and T cells in vitro with one or more antigenic cells expressing said antigenic molecule, wherein the antigen presenting cells and T cells have at least one common MHC allele; and
   (b) incubating the immune cells in vitro with a purified non-covalent complex of a heat shock protein and said antigenic molecule, whereby T cells reactive to the antigenic molecule are generated.

14. A method for generating T cells reactive to an antigenic molecule comprising:
   (a) immunizing an animal with one or more antigenic cells expressing said antigenic molecule;
   (b) obtaining immune cells from the animal, said immune cells comprising T cells;
   (c) incubating the immune cells with antigen presenting cells pulsed with a purified non-covalent complex of a heat shock protein and the antigenic molecule, wherein the antigen presenting cells and immune cells have at least one common MHC allele; and
   (d) repeating said incubating step at least one, by adding said antigen presenting cells pulsed with a purified non-covalent complex of a heat shock protein and the antigenic molecule to said incubated cells resulting from step (c),
whereby T cells reactive to the antigenic molecule are generated.

15. The method as in any one of claims 1–4, 5 or 6–14 in which the immune cells are enriched for CD4+ lymphocytes and antigen presenting cells.

16. The method as in any one of claims 1–4, 5 or 6–14, wherein the antigenic molecule is a tumor-specific or tumor-associated antigen.

17. The method as in any one of claims 1–4, 5 or 6–14, wherein the antigenic molecule is derived from a cancer cell.

18. the method as in any one of claims 1–4, 5 or 6–14, wherein the antigenic molecule is derived from a cancer cell selected from the group consisting of sarcoma, carcinoma, leukemia, lymphoma, myeloma, prostate cancer, breast cancer, and colon cancer cells.

19. The method as in any of claims 1–4, 5 or 6–14, wherein the antigenic molecule is recombinantly produced.

20. The method of claim 10, 11, 12, 13, or 14 in which the antigenic cells are human cells.

21. The method as in any one of claims 1–4, 5 or 6–14, wherein the immune cells are human cells.

22. The method as in any one of claims 1–4, 5 or 6–14, wherein the immune cells are peripheral blood lymphocytes or whole blood leukocytes.

23. The method of claim 10, 11, 12, 13, or 14, wherein the immune cells and antigenic cells are derived from the same human.

24. The method as in any one of claims 1–4, 5 or 6–14 further comprising recovering from a cell culture the T cells reactive to the antigenic molecule.

25. The method as in any one of claims 1–4, 5 or 6–14, wherein the non-covalent complex of heat shock protein and antigenic molecule is obtained from antigenic cells.

26. The method as in any one of claims 1–4, 5 or 6–14, wherein the non-covalent complex of heat shock protein and antigenic molecule is produced in vitro.

27. The method as in any one of claims 1–4, 5 or 6–14 further comprising restimulating the immune cells, in vitro, at least once with a non-covalent complex of a heat shock protein and an antigenic molecule.

28. The method as in any one of claims 1–4, 5 or 6–14, wherein the heat shock protein is HSP60, HSP70, HSP90, HSP100, or gp96.

29. The method as in any one of claims 1–4, 5 or 6–14, wherein the heat shock protein is a member of the small heat shock protein (sHSP) family.

30. The method of claim 17 wherein the cancer cell has been induced in vitro to become cancerous or transformed.

31. The method as in any one of claims 1–4, 5 or 6–14 in which the antigenic molecule is derived from an infected cell.

32. The method of claim 31 wherein said infected cell is infected with a virus, a bacterium, a fungus, a parasite, or a protozoan.

33. The method as in any one of claims 1–4, 5 or 6–14 wherein the antigenic cell recombinantly expresses an antigenic molecule of a pathogen.

34. The method as in any one of claims 1–4, 5 or 6–14 wherein the antigenic cell has been infected in vitro by a pathogen.

35. The method a in any one of claims 1–4, or 6–14, said method further comprising: repeating said incubating step at least once, by incubating said purified non-covalent complex and said antigen presenting cells to said incubated cells resulting from said incubating step.

* * * * *

UNITED STATES PATENT AND TRADEMARK OFFICE
CERTIFICATE OF CORRECTION

PATENT NO. : 6,451,316 B1
DATED : September 17, 2002
INVENTOR(S) : Srivastava

It is certified that error appears in the above-identified patent and that said Letters Patent is hereby corrected as shown below:

Column 33,
Line 52, replace "molecule said" with -- molecule, said --
Line 54, replace "cells with the" with -- cells from the --

Column 34,
Line 55, replace "dells" with -- cells --
Line 59, replace "hereby" with -- whereby --

Column 36,
Line 18, replace "complcx" with -- complex --
Line 44, replace "a" with -- as --
Line 57, replace "to" with -- with --

Signed and Sealed this

Twenty-seventh Day of May, 2003

JAMES E. ROGAN
*Director of the United States Patent and Trademark Office*